(12) United States Patent
Vickery et al.

(10) Patent No.: US 11,491,179 B2
(45) Date of Patent: Nov. 8, 2022

(54) ARTICLE OF MANUFACTURE COMPRISING LOCAL ANESTHETIC, BUFFER, AND GLYCOSAMINOGLYCAN IN SYRINGE WITH IMPROVED STABILITY

(71) Applicant: Urigen Pharmaceuticals, Inc., North Brunswick, NJ (US)

(72) Inventors: Dan Vickery, North Brunswick, NJ (US); Christopher Meenan, North Brunswick, NJ (US); Lowell C. Parsons, Henderson, NV (US); Andreas Meier, Cologne (DE)

(73) Assignee: Urigen Pharmaceuticals, Inc., North Brunswick, NJ (US)

( * ) Notice: Subject to any disclaimer, the term of this patent is extended or adjusted under 35 U.S.C. 154(b) by 192 days.

(21) Appl. No.: 16/604,471

(22) PCT Filed: Apr. 11, 2018

(86) PCT No.: PCT/US2018/027162
§ 371 (c)(1),
(2) Date: Oct. 10, 2019

(87) PCT Pub. No.: WO2018/191412
PCT Pub. Date: Oct. 18, 2018

(65) Prior Publication Data
US 2021/0283172 A1    Sep. 16, 2021

Related U.S. Application Data

(60) Provisional application No. 62/484,477, filed on Apr. 12, 2017.

(51) Int. Cl.
*A61P 13/10*    (2006.01)
*A61P 31/10*    (2006.01)
(Continued)

(52) U.S. Cl.
CPC ......... *A61K 31/727* (2013.01); *A61K 9/0034* (2013.01); *A61K 9/08* (2013.01);
(Continued)

(58) Field of Classification Search
None
See application file for complete search history.

(56) References Cited

U.S. PATENT DOCUMENTS 5,008,356 A    4/1991  Ishimaru et al.
5,087,677 A    2/1992  Brekner et al.
(Continued)

FOREIGN PATENT DOCUMENTS

JP    2011-195463 A    10/2011
WO    2006/076663 A2    7/2006
(Continued)

OTHER PUBLICATIONS

Unger et al., "Adsorption of xenobiotics to plastic tubing incorporated into dynamic in vitro systems used in pharmacological research—limits and progress" Biomaterials vol. 22 pp. 2031-2037 (Year: 2001).*

(Continued)

*Primary Examiner* — Eric Olson
(74) *Attorney, Agent, or Firm* — Ditthavong, Steiner & Mlotkowski

(57) ABSTRACT

An article of manufacture according to the present invention comprises a composition including a glycosaminoglycan, a local anesthetic, and a buffer packaged in a syringe or vial constructed from either glass or a plastic selected from the group consisting of cyclic olefin polymer, cyclic olefin copolymer, or high density non-nucleated polypropylene. The composition has unexpectedly improved stability on storage. The composition can be formulated for treatment of a urinary tract disease or condition, such as interstitial (Continued)

cystitis, also known as bladder pain syndrome or hypersensitive bladder syndrome.

21 Claims, 13 Drawing Sheets

(51) Int. Cl.

| | |
|---|---|
| A61K 9/00 | (2006.01) |
| A61K 9/08 | (2006.01) |
| A61K 31/167 | (2006.01) |
| A61K 31/728 | (2006.01) |
| A61K 31/737 | (2006.01) |
| A61K 31/727 | (2006.01) |
| A61K 31/216 | (2006.01) |
| A61K 47/02 | (2006.01) |
| A61K 47/18 | (2017.01) |

(52) U.S. Cl.
CPC .......... *A61K 31/167* (2013.01); *A61K 31/216* (2013.01); *A61K 31/728* (2013.01); *A61K 31/737* (2013.01); *A61K 47/02* (2013.01); *A61K 47/18* (2013.01); *A61P 13/10* (2018.01); *A61P 31/10* (2018.01)

(56) References Cited

U.S. PATENT DOCUMENTS

| | | | |
|---|---|---|---|
| 5,304,596 | A | 4/1994 | Moriya et al. |
| 5,324,801 | A | 6/1994 | Brekner et al. |
| 5,331,057 | A | 7/1994 | Brekner et al. |
| 5,422,409 | A | 6/1995 | Brekner et al. |
| 5,559,199 | A | 9/1996 | Abe et al. |
| 5,795,945 | A | 8/1998 | Natori |
| 5,820,605 | A | 10/1998 | Zdeb et al. |
| 6,065,270 | A | 3/2000 | Reinhard et al. |
| 6,090,888 | A | 7/2000 | Khananian et al. |
| 6,197,894 | B1 | 3/2001 | Sunaga et al. |
| 6,388,032 | B1 | 5/2002 | Yamaura et al. |
| 6,627,714 | B2 | 9/2003 | Yamamoto et al. |
| 6,639,021 | B2 | 10/2003 | Oshima et al. |
| 6,844,403 | B2 | 1/2005 | Oshima et al. |
| 6,908,970 | B2 | 6/2005 | Tsunogae et al. |
| 6,992,154 | B2 | 1/2006 | Oshima et al. |
| 7,041,087 | B2 | 5/2006 | Henderson et al. |
| 7,122,239 | B2 | 10/2006 | Bennei, I et al. |
| 7,202,312 | B2 | 4/2007 | Choi et al. |
| 7,258,930 | B2 | 8/2007 | Rivett et al. |
| 7,414,039 | B2 | 8/2008 | Parsons |
| 7,468,417 | B2 | 12/2008 | Jang et al. |
| 7,648,937 | B2 | 1/2010 | Yoon et al. |
| 7,662,445 | B2 | 2/2010 | Nagura et al. |
| 7,740,792 | B2 | 6/2010 | Haury et al. |
| 7,766,882 | B2 | 8/2010 | Sudo et al. |
| 7,814,713 | B2 | 10/2010 | Yoon et al. |
| 7,838,088 | B2 | 11/2010 | Suzuki et al. |
| 7,854,873 | B2 | 12/2010 | Heidari et al. |
| 7,964,680 | B2 | 6/2011 | Choi et al. |
| 7,985,188 | B2 | 7/2011 | Felts et al. |
| 7,989,570 | B2 | 8/2011 | Chun et al. |
| 8,084,563 | B2 | 12/2011 | Sakagami et al. |
| 8,148,472 | B1 | 4/2012 | Baugh et al. |
| 8,158,732 | B2 | 4/2012 | Wakatsuki et al. |
| 8,293,674 | B2 | 10/2012 | Chung et al. |
| 8,303,540 | B2 | 11/2012 | Shue et al. |
| 8,344,070 | B2 | 1/2013 | Squire et al. |
| 8,357,795 | B2 | 1/2013 | Lebreton et al. |
| 8,398,600 | B2 | 3/2013 | Hirokane et al. |
| 8,541,621 | B2 | 9/2013 | Shin et al. |
| 8,627,970 | B2 | 1/2014 | Macy et al. |
| 8,637,128 | B2 | 1/2014 | Jemelin |
| 8,679,068 | B2 | 3/2014 | Young |
| 8,721,603 | B2 | 5/2014 | Lundquist |
| 8,747,726 | B2 | 6/2014 | Haury et al. |
| 8,883,925 | B2 | 11/2014 | Kizu et al. |
| 8,939,940 | B2 | 1/2015 | Haury et al. |
| 8,946,366 | B2 | 2/2015 | Yoo et al. |
| 9,056,938 | B2 | 6/2015 | Sunaga et al. |
| 9,151,988 | B2 | 10/2015 | Yoo et al. |
| 9,163,113 | B2 | 10/2015 | Choi et al. |
| 9,206,278 | B2 | 12/2015 | Yoshida et al. |
| 9,220,631 | B2 | 12/2015 | Sigg et al. |
| 9,302,050 | B2 | 4/2016 | Creaturo et al. |
| 9,359,588 | B2 | 6/2016 | Smith |
| 9,381,687 | B2 | 7/2016 | Felts et al. |
| 9,533,103 | B2 | 1/2017 | Okihara |
| 9,554,986 | B2 | 1/2017 | Harvey |
| 2008/0300219 | A1 | 12/2008 | Parsons |
| 2010/0028438 | A1 | 2/2010 | Lebreton |
| 2012/0196830 | A1 | 8/2012 | Parsons |
| 2014/0194380 | A1 | 7/2014 | Parsons |
| 2014/0373485 | A1 | 12/2014 | Okada et al. |
| 2015/0038457 | A1 | 2/2015 | Bourdon et al. |
| 2015/0297492 | A1* | 10/2015 | Yu .............. A61K 8/41 514/626 |
| 2021/0346323 | A1* | 11/2021 | Matsuoka ............ A61J 1/1468 |

FOREIGN PATENT DOCUMENTS

| | | |
|---|---|---|
| WO | 2007/073397 A1 | 6/2007 |
| WO | 2010015900 A1 | 2/2010 |
| WO | 2011023355 A2 | 3/2011 |
| WO | 2012094515 A1 | 7/2012 |
| WO | 2012104419 A1 | 8/2012 |
| WO | 2013166014 A1 | 11/2013 |
| WO | 2014171986 A1 | 10/2014 |
| WO | 2015015407 A1 | 2/2015 |
| WO | 2015043757 A1 | 4/2015 |

OTHER PUBLICATIONS

Takakura et al., "Adsorption of Lidocaine into a Plastic Infusion Balloon" Anesth Analg vol. 91 pp. 192-194 (Year: 2000).*
Pascuet et al., "Buffered Lidocaine Hydrochloride Solution With and Without Epinephrine: Stability in Polypropylene Syringes" JCPH vol. 62 No. 5 pp. 375-380 (Year: 2009).*
Storms et al., "Stability of Lidocaine Hydrochloride Injection as Ambient Temperature and 4C in Polypropylene Syringes" International Journal of Pharmaceutical Compounding vol. 6 No. 5 pp. 388-390 (Year: 2002).*
"Eltex®MED Polyethylene and Polypropylene Resins for Medical and Pharmaceutical Applications", published in INEOS Olefins and Polymers Europe, Oct. 2014, 2 pages.

* cited by examiner

| Test | Specification | Start unsterile | Start sterile | 1 month | 2 months | 3 months | 6 months |
|---|---|---|---|---|---|---|---|
| Appearance manufactured good | 20 mL syringes made of cyclo olefin polymer with grey plunger and tip caps | compliance | compliance | compliance | compliance | compliance | compliance |
| Appearance filled (sterile) good | colourless clear solution | compliance | compliance | compliance | compliance | compliance | compliance |
| pH value | 7.4 +/- 0.2 | 7,46 | 7,42 | 7,38 | 7,44 | 7,41 | 7,41 |
| Assay lidocaine HCl [g/100g] | 1.26 - 1.40 g / 100 g | 1,34 | 1,34 | 1,33 | 1,33 | 1,33 | 1,34 |
| Loss of lidocaine HCl | | - | 0,00% | 0,75% | 0,75% | 0,75% | 0,00% |
| Assay DMA [ppm] | max. 8 ppm | 0.00 | 0.56 | 0.67 | 0.54 | 0.51 | 0.63 |
| Impurity B | | 0.000 | 0.016 | 0.012 | 0.007 | 0.009 | 0.024 |
| Impurity 5 | | 0.000 | 0.014 | 0.012 | 0.021 | 0.019 | 0.028 |
| Sum Impurities | max. 0.75 | 0.000 | 0.030 | 0.024 | 0.028 | 0.029 | 0.053 |
| | Testing guideline: | MV-VZ-1907 | MV-VZ-1907 | MV-VZ-1907 | MV-VZ-1907 | MV-VZ-1907 | MV-VZ-1907 |
| | Tester: | LBL | LBL | LBL | LBL | LBL | LBL |

FIGURE 3

| Test | Specification | Start unsterile | Start sterile | 1 month | 2 months | 3 months | 6 months |
|---|---|---|---|---|---|---|---|
| Appearance manufactured good | 20 mL syringes made of cyclo olefin polymer with grey plunger and tip caps | compliance | compliance | compliance | compliance | compliance | compliance |
| Apperance filled (sterile) good | colourless clear solution | compliance | compliance | compliance | compliance | compliance | compliance |
| pH value | 7.4 +/- 0.2 | 7.46 | 7.42 | 7.37 | 7.39 | 7.39 | 7.36 |
| Assay lidocaine HCl [g/100g] | 1.26 - 1.40 g / 100 g | 1.34 | 1.34 | 1.33 | 1.31 | 1.30 | 1.29 |
| Loss of lidocaine HCl |  | - | 0.00% | 0.75% | 2.24% | 2.99% | 3.73% |
| Assay DMA [ppm] | max. 8 ppm | 0.00 | 0.56 | 0.72 | 0.82 | 1.00 | 1.41 |
| Impurity B |  | 0.000 | 0.016 | 0.028 | 0.046 | 0.057 | 0.115 |
| Impurity 5 |  | 0.000 | 0.014 | 0.028 | 0.043 | 0.048 | 0.079 |
| Sum Impurities | max. 0.75 | 0.000 | 0.030 | 0.056 | 0.089 | 0.105 | 0.194 |
|  | Testing guideline: | MV-VZ-1907 | MV-VZ-1907 | MV-VZ-1907 | MV-VZ-1907 | MV-VZ-1907 | MV-VZ-1907 |
|  | Tester: | LBL | LBL | LBL | LBL | LBL | LBL |

FIGURE 4

| Test | Specification | Start unsterile | Start sterile | 1 month | 2 months | 3 months | 6 months |
|---|---|---|---|---|---|---|---|
| Appearance manufactured good | 20 ml syringes made of polypropylene with blue plunger and tip caps | compliance | compliance | compliance | compliance | compliance | compliance |
| Appearance filled (sterile) good | colourless clear solution | compliance | compliance | compliance | compliance | compliance | compliance |
| pH value | 7.4 +/- 0.2 | 7,46 | 7,3 | 7,26 | 7,26 | 7,28 | 7,26 |
| Assay lidocaine HCl [g/100g] | 1.26 - 1.40 g / 100 g | 1,34 | 1,23 | 1,22 | 1,21 | 1,21 | 1,22 |
| Loss of lidocaine HCl | | - | 8.21% | 8.95% | 9.70% | 9.70% | 8.95% |
| Assay DMA [ppm] | max. 8 ppm | 0.00 | 0.52 | 0.33 | 0.44 | 0.34 | 0.40 |
| Impurity B | | 0.000 | 0.017 | 0.015 | 0.014 | 0.008 | 0.021 |
| Impurity 5 | | 0.000 | 0.018 | 0.015 | 0.017 | 0.017 | 0.023 |
| Sum Impurities | max. 0.75 | 0.000 | 0.035 | 0.030 | 0.031 | 0.026 | 0.044 |
| Testing guideline: Tester: | | MV-VZ-1907 LBL | MV-VZ-1907 LBL | MV-VZ-1907 LBL | MV-VZ-1907 LBL | MV-VZ-1907 LBL | MV-VZ-1907 LBL |

FIGURE 5

| Test | Specification | Start unsterile | Start sterile | 1 month | 2 months | 3 months | 6 months |
|---|---|---|---|---|---|---|---|
| Appearance manufactured good | 20 mL syringes made of polypropylene with blue plunger and tip caps | compliance | compliance | compliance | compliance | compliance | compliance |
| Apperance filled (sterile) good | colourless clear solution | compliance | compliance | compliance | compliance | compliance | compliance |
| pH value | 7.4 +/- 0.2 | 7.46 | 7.30 | 7.25 | 7.24 | 7.23 | 7.17 |
| Assay lidocaine HCl [g/100g] | 1.26 - 1.40 g / 100 g | 1.34 | 1.23 | 1.22 | 1.18 | 1.20 | 1.16 |
| Loss of lidocaine HCl | | - | 8.21% | 8.95% | 11.94% | 10.45% | 13.43% |
| Assay DMA [ppm] | max. 8 ppm | 0.00 | 0.52 | 0.42 | 0.58 | 0.61 | 0.94 |
| Impurity B | | 0.000 | 0.017 | 0.027 | 0.040 | 0.049 | 0.103 |
| Impurity 5 | | 0.000 | 0.018 | 0.029 | 0.040 | 0.052 | 0.080 |
| Sum Impurities | max. 0.75 | 0.000 | 0.035 | 0.055 | 0.080 | 0.101 | 0.183 |
| | Testing guideline: Tester: | MV-VZ-1907 LBL | MV-VZ-1907 LBL | MV-VZ-1907 LBL | MV-VZ-1907 LBL | MV-VZ-1907 LBL | MV-VZ-1907 LBL |

FIGURE 6

ARTICLE OF MANUFACTURE COMPRISING LOCAL ANESTHETIC, BUFFER, AND GLYCOSAMINOGLYCAN IN SYRINGE WITH IMPROVED STABILITY

CROSS-REFERENCE TO RELATED APPLICATION

This application claims the benefit of U.S. Provisional Application Ser. No. 62/484,477 by Dr. Dan Vickery et al., entitled "Article of Manufacture Comprising Local Anesthetic, Buffer, and Glycosaminoglycan in Plastic Syringe with Improved Stability," and filed on Apr. 12, 2017, the contents of which are incorporated herein in their entirety by this reference.

FIELD OF THE INVENTION

The present invention is directed to an article of manufacture comprising a local anesthetic, a buffer, and a glycosaminoglycan in a syringe or vial with improved stability, typically in combination with terminal sterilization of the article or manufacture.

BACKGROUND OF THE INVENTION

Interstitial cystitis (IC), also frequently known as bladder pain syndrome or hypersensitive bladder syndrome, is a chronic progressive disorder of the lower urinary tract that causes urinary urgency and frequency and/or pelvic pain. American Urology Association defines IC/BPS as "An unpleasant sensation (pain, pressure, discomfort) perceived to be related to the urinary bladder, associated with lower urinary tract symptoms of more than six weeks duration, in the absence of infection or other identifiable causes." For many years, urologists regarded IC/BPS as a rare disease for which they had no broadly effective treatment. In fact, the condition is quite common. In 1999, prevalence in the United States was estimated at 750,000 cases (Curhan, et al. J Urol 161(2):549-552 (1999)). However current estimates from the RAND Interstitial Cystitis Epidemiology (RICE) study suggests the true prevalence of IC/BPS is estimated to be 2.7% to 6.53% (approximately 3.3 to 7.9 million US women age 18 or older) and 2.9% to 4.2% (approximately 2.0 to 4.6 million US men age 18 or older) Berry S H et al. J Urol 2011; 186: 540. And Suskind A M et al. J Urol 2013; 189: 141 (. In addition overactive bladder, urethral syndrome, prostatitis, and gynecologic chronic pelvic pain syndrome comprises millions of patients that also result in bladder symptoms of urgency, frequency, incontinence and or pelvic pain with no effective therapy and all these syndromes share similar symptoms and likely a common pathophysiology with traditionally diagnosed IC (Parsons, C L Int Br J Urol December, 2010); there are no broadly effective treatments for these conditions.

Therefore, treatments that would both benefit a larger portion of the patient population, provide immediate relief of symptoms without causing additional pain, without requiring extensive alterations in diet, and further provide reversal of the disease process over time are necessary.

Compositions and methods for the treatment of interstitial cystitis are described in U.S. Pat. No. 7,414,039 to Parsons, issued Aug. 19, 2008 and entitled "Interstitial Therapy for Immediate Symptom Relief and Chronic Therapy in Interstitial Cystitis," and in United States Patent Application Publication No. 2008/0300219 by Parsons, published Dec. 4, 2008 and entitled "Novel Interstitial Therapy for Immediate Symptom Relief and Chronic Therapy in Interstitial Cystitis," both of which are incorporated herein in their entirety by this reference, as well as PCT Patent Application Publication No. WO 2006/07663 by Flashner et al., published Jul. 20, 2006 and entitled "Kits and Improved Compositions for Treating Lower Urinary Tract Disorders," and PCT Patent Application Publication No. WO 2007/073397 by Flashner et al., published Jun. 28, 2007 and entitled "Kits and Improved Compositions for Treating Lower Urinary Tract Disorders," both of which are incorporated herein in their entirety by this reference. In general, the compositions disclosed in this issued patent and these published patent applications comprise a local anesthetic, typically lidocaine, a glycosaminoglycan, typically a heparinoid, more typically heparin, and a buffer. The composition is instilled into the urinary bladder. The buffer is typically phosphate buffer, although, as described below, other buffers, such as bicarbonate buffer or Tris buffer, can be used. A particularly preferred phosphate buffer is sodium phosphate buffer.

Alkalinized lidocaine and heparin can be used to successfully treat bladder symptoms such as, but not limited to, urinary frequency, urgency, incontinence and bladder generated pain. Pain generated by the urinary bladder (a visceral organ) is not always perceived to be arising from the bladder. Pain can be referred anywhere from the navel to the knees and will also refer from the lumbar area down the buttocks to the legs and often has no relation to bladder filling or emptying. Consequently the origin of pelvic pain may not be recognized to be from the bladder. These bladder symptoms can be seen in a variety of "clinical syndromes" which may actually be all from one disease process: a dysfunctional epithelium (Parsons, C L Int Br J Urol, December 2010)). Nonetheless all these syndromes that can generate bladder symptoms that can be successfully treated with this solution, including, but not limited to, overactive bladder, interstitial cystitis, urethral syndrome in women, recurrent lower urinary tract infection, prostatitis (male chronic pelvic pain syndrome), radiation cystitis, chemical cystitis, gynecologic chronic pelvic pain syndrome (e.g. endometriosis, vulvodynia, vulvovaginitis, yeast vaginitis).

However, there is a problem in mixing these compounds, as the wrong balance may result in the precipitation of lidocaine and loss of efficacy. Lidocaine when exposed to pH's at or above 7.0 will de-ionize and absorb through lipid membranes such as the bladder epithelium. As a result, the absorbed lidocaine will anesthetize the bladder nerves and relieve bladder symptoms noted above. The heparin will "coat" the bladder wall and inhibit the diffusion of urine solutes that provoke the bladder symptoms in the first place. So the combination provides prolonged relief of bladder symptoms (Parsons, Urology 2003). However, mixing the heparin, lidocaine, and buffering agent has to be done in an exact way to prevent the precipitation of the lidocaine since lidocaine will precipitate at pH values above 7 depending on the conditions. The precipitation of lidocaine reduces its bioavailability and reduces the efficacy of the composition.

However, even if the composition is prepared in a way that prevents immediate precipitation of the lidocaine on the formation of the composition involving the mixing of the glycosaminoglycan, the buffer, and the local anesthetic, the storage and transportation of the composition requires long-term stability. One factor in the loss of stability of the lidocaine and thus the loss of lidocaine from the composition is the interaction of the alkalinized lidocaine with syringe components. Lidocaine becomes bound to the syringe after sterilization. In the absence of such long-term stability, there is a significant risk that a patient will be administered a dosage of one or more of the components of the composition that will not have the desired clinical effect. Therefore, there is a particular need for compositions of manufacture that include the composition and are stable, and can be transported and stored in a form that is ready for administration to a patient. In addition, there is a need for such a composition of matter that can withstand sterilization without a significant decrease in stability.

SUMMARY OF THE INVENTION

An article of manufacture comprising a composition including a glycosaminoglycan, a local anesthetic, and a buffer packaged in a syringe or vial constructed from a material selected from glass and a high density plastic polymer. Typically, the high density plastic polymer is a plastic selected from the group consisting of cyclic olefin polymer, cyclic olefin copolymer, high density polyethylene, and high density non-nucleated polypropylene meets these needs and provides improved stability of the composition in a container such that it is suitable for administration to the urinary tract of a patient suffering from interstitial cystitis (bladder pain syndrome or hypersensitive bladder syndrome) or another urinary tract disease or disorder.

In general, the present invention is directed to an article of manufacture comprising a composition including a glycosaminoglycan, a local anesthetic, and a buffer packaged in a syringe or vial constructed from glass or a high density plastic polymer. Typically, the high density plastic polymer is selected from the group consisting of cyclic olefin polymer and cyclic olefin copolymer, high density polyethylene, and high density non-nucleated polypropylene.

In one alternative, the interior of the syringe barrel can be coated to reduce deposition of the anesthetic on the syringe surface.

Typically, the glycosaminoglycan is a heparinoid. Preferably, the heparinoid is selected from the group consisting of heparin, chondroitin sulfate, heparan sulfate, hyaluronic acid, keratan sulfate, dermatan sulfate, hyaluronan, sodium pentosanpolysulfate, dalteparin and enoxaparin. Particularly preferred heparinoids include heparin, heparan sulfate, chondroitin sulfate, hyaluronic acid, and sodium pentosanpolysulfate. A more particularly preferred heparinoid is heparin, such as heparin sodium. The heparin can be a heparin that has a molecular weight from about 2,000 daltons to about 8,000 daltons; alternatively, the heparin can be a heparin that has a molecular weight of from about 8,000 daltons to about 40,000 daltons.

Typically, when the glycosaminoglycan is heparin, a unit dose of the composition included in the article of manufacture comprises from about 1000 units of heparin to about 250,000 units of heparin per unit dose of the composition. Preferred quantities of heparin per unit dose of the composition include 40,000 units, 50,000 units, and 60,000 units of heparin. Typically, when the glycosaminoglycan is sodium pentosanpolysulfate, the composition comprises from about 1 mg to about 600 mg of sodium pentosanpolysulfate per unit dose of the composition. Typically, when the glycosaminoglycan is heparan sulfate, the composition comprises from about 0.5 mg to about 10,000 mg of heparan sulfate per unit dose of the composition. Typically, when the glycosaminoglycan is hyaluronic acid, the composition comprises from about 5 mg to about 600 mg of hyaluronic acid per unit dose of the composition. Typically, when the glycosaminoglycan is chondroitin sulfate and the composition comprises from about 1 mg to about 10,000 mg of chondroitin sulfate per unit dose of the composition.

Typically, the local anesthetic is selected from the group consisting of benzocaine, lidocaine, tetracaine, bupivacaine, etidocaine, mepivacaine, pramoxine, prilocaine, procaine, chloroprocaine, oxyprocaine, proparacaine, ropivacaine, dyclonine, dibucaine, propoxycaine, dexivacaine, diamocaine, hexylcaine, levobupivacaine, pyrrocaine, risocaine, rodocaine, and pharmaceutically acceptable derivatives and bioisosteres thereof, and a combination thereof. Preferred local anesthetics include lidocaine, bupivacaine, mepivacaine, benzocaine, tetracaine, etidocaine, prilocaine, and dibucaine. More preferred local anesthetics include lidocaine, bupivacaine, and mepivacaine. A particularly preferred local anesthetic is lidocaine, such as lidocaine hydrochloride. When the local anesthetic is lidocaine, typically a unit dose of the composition included in the article of manufacture comprises a quantity of lidocaine of from about 10 mg to about 400 mg of lidocaine per unit dose of the composition.

Typically, the buffer is selected from the group consisting of phosphate buffer, bicarbonate buffer, Tris (Tris(hydroxymethyl)aminomethane) buffer, MOPS buffer (3-(N-morpholino)propanesulfonic acid), HEPES (N-(2-hydroxyethyl)piperazine-N-(2-ethanesulfonic acid) buffer, ACES (2-[(2-amino-2-oxoethyl)amino]ethanesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS (N-(2-hydroxyethylpiperazine)-N'-(3-propanesulfonic acid) buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropaneulfonic acid) buffer, TAPS (N-tris[hydroxymethyl)methyl-3-aminopropanesulfonic acid) buffer; TAPSO (3-[N-tris(hydroxymethyl)methylamino]-2-hydroxy-
propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, and a combination thereof. Preferred buffers include phosphate buffer, bicarbonate buffer, Tris buffer, and a combination thereof. A particularly preferred buffer is phosphate buffer. A more particularly preferred buffer is sodium phosphate buffer.

In one alternative, the composition included in the article of manufacture comprises an additional component selected from the group consisting of:

(1) an osmolar component that provides an isotonic or nearly isotonic solution compatible with human cells and blood;

(2) a compound that enables persistence of the composition to the surface of the bladder epithelium in a quantity sufficient to treat, ameliorate, or prevent a lower urinary tract disorder;

(3) an antibacterial agent in a quantity sufficient to treat, ameliorate, or prevent a lower urinary tract disorder;

(4) an antifungal agent in a quantity sufficient to treat, ameliorate, or prevent a lower urinary tract disorder;

(5) a vasoconstrictor in a quantity sufficient to treat, ameliorate, or prevent a lower urinary tract disorder;

(6) a preservative; and (7) an anti-inflammatory agent.

Typically, the pH of the composition included in the article of manufacture is from about 6.8 to about 8.3. Preferably, the pH of the composition included in the article of manufacture is from about 7.2 to about 7.6. More preferably, the pH of the composition included in the article of manufacture is about 7.5.

Typically, the composition included in the article of manufacture is formulated for treating a lower urinary tract disorder selected from the group consisting of bacterial cystitis, fungal/yeast cystitis, vulvar vestibulitis, vulvodynia, dyspareunia, urethral syndrome, and endometriosis in women; prostatitis and chronic pelvic pain syndrome in men; and radiation-induced cystitis, chemotherapy-induced cystitis, interstitial cystitis, and overactive bladder in men or women. In particular, the composition included in the article of manufacture is formulated for treating interstitial cystitis (also known as bladder pain syndrome or hypersensitive bladder syndrome).

In one alternative, the syringe or vial is constructed of glass. In another alternative, the syringe or vial is constructed of cyclic olefin polymer (COP) plastic. In yet another alternative, the syringe or vial is constructed of cyclic olefin copolymer (COC) plastic. In still another alternative, the syringe or vial is constructed of high density polyethylene. In still another alternative, the syringe or vial is constructed of high density non-nucleated polypropylene. In one alternative, when the container is a syringe, the syringe has a volume of 20 mL; syringes of other volumes can be used.

In one alternative, the composition included in the article of manufacture is prepared as follows in purified water with the specified concentrations of ingredients:

(1) 16.67 g/L of heparin sodium;

(2) 13.33 g/L of lidocaine hydrochloride;

(3) 10.03 g/L of $Na_2HPO_4.12H_2O$ to produce a concentration of 0.028 M; and (4) 0.02 N NaOH as needed to adjust pH.

BRIEF DESCRIPTION OF THE DRAWINGS

These and other features, aspects, and advantages of the present invention will become better understood with reference to the following description, appended claims, and accompanying drawings where:

FIG. 3 shows the results of stability storage tests at 25° C./60% RH in COP syringes in Example 2.

FIG. 4 shows the results of stability storage tests at 40° C./75% RH in COP syringes in Example 2.

FIG. 5 shows the results of stability storage tests at 25° C./60% RH in PP syringes in Example 2.

FIG. 6 shows the results of stability storage tests at 40° C./75% RH in PP syringes in Example 2.

DETAILED DESCRIPTION OF THE INVENTION

Figure 1:
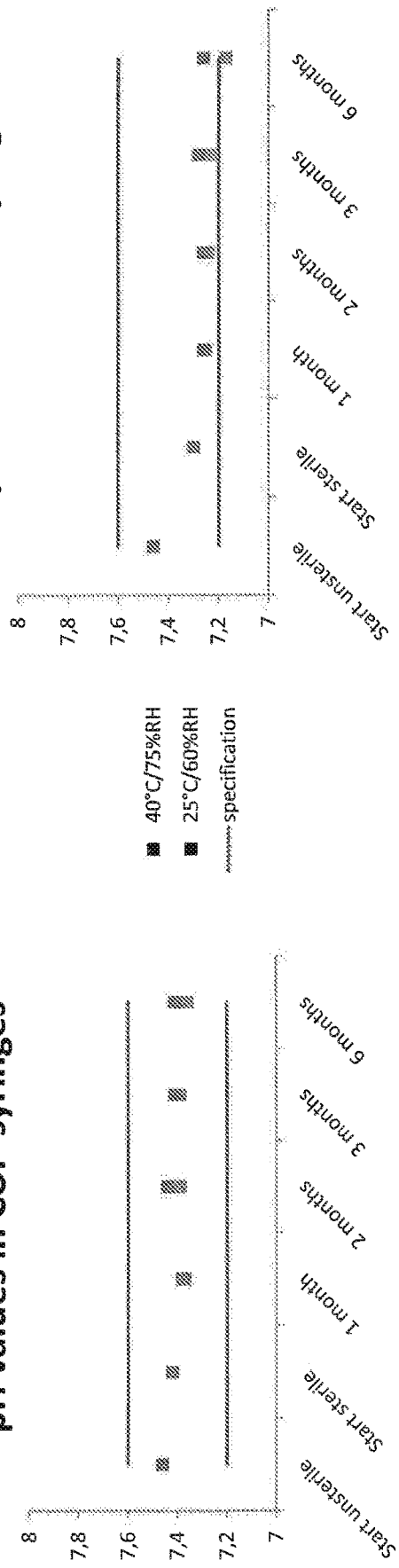
FIG. 1 shows the results for stability of pH values in cyclic olefin polymer (COP) syringes (left panel) and polypropylene (PP) syringes (right panel) for up to 6 months in Example 2.

In general, the present invention comprises an article of manufacture comprising a composition including a glycosaminoglycan, a local anesthetic, and a buffer packaged in a syringe or vial constructed from a glass or a plastic selected from the group consisting of cyclic olefin polymer, cyclic olefin copolymer, high density polyethylene, and high density non-nucleated polypropylene. Typically, as detailed below, the glycosaminoglycan is a heparinoid. Preferably, as detailed below, the heparinoid is a heparin. Typically, as detailed below, the local anesthetic is lidocaine. Typically, as detailed below, the buffer is phosphate buffer, particularly sodium phosphate buffer. However, other buffers, including but not limited to bicarbonate buffer and Tris buffer, can alternatively be used.

I. The Composition Including the Glycosaminoglycan, The Local Anesthetic, and the Buffer The composition included in the article of manufacture includes a glycosaminoglycan, a local anesthetic, and a buffer. As detailed below, other ingredients can also be included in the composition.

The glycosaminoglycan is present in the composition in a quantity sufficient to treat a urinary tract disease or condition such as interstitial cystitis (also known as bladder pain syndrome (BPS) or bladder hypersensitivity syndrome (BHS)). The local anesthetic is also present in the composition in a quantity sufficient to treat a urinary tract disease or condition such as interstitial cystitis (also BPS or BHS). The buffer is present in the composition in a quantity such that from about 2% to about 45% of the local anesthetic is present in the composition in the free base (uncharged) form rather than the protonated (charged) form.

Typically, the glycosaminoglycan is a heparinoid. As used herein, "heparinoid" refers to any molecule comprising a glycosaminoglycan which refers to a molecule comprising a network of long, branched chains of sugars (e.g., heparin, chondroitin sulfate, heparan sulfate, hyaluronic acid, keratan sulfate, dermatan sulfate, hyaluronan, sodium pentosanpolysulfate, and the like) and optimally further comprising smaller, nitrogen-containing molecules (e.g. low molecular weight molecules). It is not meant to limit the present invention to any one glycosaminoglycan (GAG) or source of GAG. GAG molecules include but are not limited to low molecular weight (LMW) GAGs, naturally derived GAGs, biotechnologically prepared GAGs, chemically modified GAGs, synthetic GAGs, and the like. Heparinoids can also be comprised of pentoses instead of hexoses (GAGs are comprised of hexoses) such as pentosanpolysulfate. It is not meant to limit the present invention to any one heparinoid molecule or source of heparinoid molecule. As used herein, "heparin" refers to a heterogeneous group of straight-chain anionic glycosaminoglycans, as described above, with a molecular weight ranging from 2,000 to 40,000 Da. In some embodiments, heparin is a higher molecular weight species ranging from 8,000-40,000 daltons. As used herein, "low-molecular-weight heparins" refers to a lower molecular weight (LMW) species ranging from 2,000 to 8,000 daltons. Sodium pentosanpolysulfate can range from 2,000 to 6,000 daltons. Also included within the scope of the invention are polymers such as dalteparin or enoxaparin. LMW heparins are made by enzymatic or chemical controlled hydrolysis of unfractionated heparin and have very similar chemical structure as unfractionated heparin except for some changes that may have been introduced due to the enzymatic or chemical treatment. While not intending to limit the mechanism of action of the invention's compositions, the mechanism of action of these drugs may be similar to that of full-length heparin. LMW heparins are usually isolated from bulk heparin. In one embodiment, heparin or another heparinoid is a heparin salt. As used herein, the phrases "pharmaceutically acceptable salts," "a pharmaceutically acceptable salt thereof" or "pharmaceutically accepted complex" for the purposes of this application are equivalent and refer to derivatives prepared from pharmaceutically acceptable non-toxic acids or bases including inorganic acids and bases and organic acids and bases.

Because of the negative charges of these polysaccharides due to the occurrence of sulfate groups and/or carboxylic acid groups in them, they are administered in the form of salts, with an appropriate cation to neutralize the negative charges on the acid groups. Typically, the cation is sodium. However, other physiologically tolerable counterions that do not induce urinary tract dysfunctions, such as magnesium, aluminum, calcium, ammonium, or salts made from physiologically acceptable organic bases such as, but not limited to, trimethylamine, triethylamine, morpholine, pyridine, piperidine, picoline, dicyclohexylamine, N,N'-dibenzylethylenediamine, 2-hydroxyethylamine, bis-(2-hydroxyethyl) amine, tri-(2-hydroxyethyl)amine, dibenzylpiperidine, N-benzyl-p-phenethylamine, dehydroabietylamine, N,N'-bisdehydroabietylamine, glucamine, N-methylglucamine, collidine, quinine, quinoline, and basic amino acids such as lysine and arginine, can be used. These cationic counterions can alternatively be used as the counterions with anionic buffers such as bicarbonate, as well. Sodium is typically employed as the positively-charged counterion as indicated above; accordingly, a preferred form of heparin is heparin sodium in which sodium acts as the counterion. These salts may be prepared by methods known to those skilled in the art. However, it is generally undesirable to use potassium as a counterion due to its role in the etiology of the conditions and syndromes being treated. Other polysaccharides that have the required activity include, but are not limited to, dextran sulfate and carrageenan. Other glycosaminoglycans can be used in methods according to the invention, including low molecular weight (LMW) glycosaminoglycans, naturally derived glycosaminoglycans, biotechnologically prepared glycosaminoglycans, chemically modified glycosaminoglycans, and synthetic glycosaminoglycans and linear anionic polysaccharides comprised of pentoses. Reference to a heparinoid that possesses a negative charge at physiological pH, such as heparin, without specific reference to a counterion, is to be understood as including all possible counterions that do not interfere with the physiological activity of the heparin or other components of the composition and do not create incompatibility with any other components of the composition.

In some embodiments, a heparinoid comprises a heparin-like molecule (e.g. heparan sulfate). For example, a heparin-like molecule such as heparan sulfate is a glycocosaminoglycan with a structure similar to heparin with the difference being that heparan sulfate has undergone less polymerization than heparin and so has more glucuronic acid and N-acetyl glucosamine than heparin. Heparan sulfate contains fewer sulfate groups, so is somewhat less acidic. Heparin exists in a variety of forms characterized by different degrees of sulfation. Typically, heparin has a molecular weight of from about 2 kDa to about 40 kDa. Heparin and heparan sulfate are both characterized by repeating units of disaccharides containing a uronic acid (glucuronic or iduronic acid) and glucosamine, which is either N-sulfated or N-acetylated. The sugar residues may be further O-sulfated at the C-6 and C-3 positions of the glucosamine and the C-2 position of the uronic acid. There are at least 32 potential unique disaccharide units in this class of compounds. Five examples of sugars occurring in heparin are: (1) α-L-iduronic acid 2-sulfate; (2) 2-deoxy-2-sulfamino-α-D-glucose 6-sulfate; (3) β-D-glucuronic acid; (4) 2-acetamido-2-deoxy-α-D-glucose; and (5) α-L-iduronic acid.

In one embodiment, heparin contains at least 130 USP units per mg. Heparin is measured by its specific anticoagulation activity in units; either USP units or international units (IU) are specified in stating the activity of heparin. As used herein, "USP unit" refers to the quantity of heparin that prevents 1.0 ml of citrated sheep plasma from clotting for 1 hour after the addition of 0.2 ml of 1% $CaCl_2$ at 20° C. when compared to a USP reference standard (defined as units/ml). As used herein, "IU" refers to the quantity of heparin that is active in assays as established by the Fifth International standard for Unfractionated Heparin (WHO-5) (defined as International Units/ml) (Linhardt, R. J. & Gunay, N. S. (1999) Semin Thromb Hemost 25, 5-16.). However, it is also possible, and preferred in some embodiments, to specify the heparin concentration in terms of milligrams: typically, 1 mg of heparin is approximately equivalent to 200 units.

Particularly preferred heparinoids for use in methods according to the present invention and compositions prepared by those methods include heparin and sodium pentosanpolysulfate. A most particularly preferred heparinoid for use in methods according to the present invention and compositions prepared by those methods is heparin. A preferred form of heparin is heparin sodium, although, as described above, other counterions can be used. The quantity of heparin in compositions prepared according to methods of the present invention can range from about 1000 units to about 250,000 units per unit dose of the composition; any intermediate quantity of heparin, such as, but not limited to, 1,000 units, 5,000 units, 10,000 units, 15,000 units, 20,000 units, 25,000 units, 30,000 units, 35,000 units, 40,000 units, 45,000 units, 50,000 units, 55,000 units, 60,000 units, 65,000 units, 70,000 units, 75,000 units, 80,000 units, 85,000 units, 90,000 units, 95,000 units, 100,000 units, 110,000 units, 120,000 units, 130,000 units, 140,000 units, 150,000 units, 160,000 units, 170,000 units, 180,000 units, 190,000 units, 200,000 units, 210,000 units, 220,000 units, 230,000 units, 240,000 units, or 250,000 units per unit dose of the composition can be used. As used herein, a "unit dose" refers to the dosage of heparin or other component of a composition according to the present invention that is normally administered in a single treatment. As expressed in milligrams, these quantities of heparin range from about 0.5 mg to about 1250 mg per unit dose, including but not limited to 1 mg, 5 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, or 1250 mg. Suitable quantities of heparinoids other than heparin can be determined by one of ordinary skill in the art based on the molecular weight of the heparinoid to be used. Typically, the concentration of the heparin of the composition included in the article of manufacture is from about 1,000 units of heparin per milliliter to about 6,000 units of heparin per milliliter of the composition. The concentration of the heparin of the composition included in the article of manufacture can be selected from the group consisting of 1,000 units, 1,500 units, 2,000 units, 2,500 units, 3,000 units, 3,500 units, 4,000 units, 4,500 units, 5,000 units, 5,500 units, and 6,000 units per milliliter of the composition.

The quantity of heparinoid in the composition can vary depending on the subject, the severity and course of the disease, the subject's health, the response to treatment, pharmacokinetic considerations such as liver and kidney function, and the judgment of the treating physician. Accordingly, a number of compositions including differing quantities of heparin per unit dose can be prepared by methods according to the present invention.

In accordance with the practice of the invention, merely by way of example, when the heparinoid is sodium pentosanpolysulfate, the amount of heparinoid in the composition may be about 1 mg to about 600 mg of sodium pentosanpolysulfate per unit dose (for example about 100 mg to about 600 mg per unit dose of sodium pentosanpolysulfate). In accordance with the practice of the invention, merely by way of example, when the heparinoid is heparan sulfate, the amount of heparinoid in the composition may be about 0.5 mg to about 10,000 mg of heparan sulfate per unit dose (for example about 100 mg to about 300 mg per unit dose of heparan sulfate). In accordance with the practice of the invention, merely by way of example, when the heparinoid is hyaluronic acid, the amount of heparinoid in the composition may be about 5 mg to about 600 mg of hyaluronic acid per unit dose (for example about 10 mg to about 100 mg per unit dose of hyaluronic acid). In accordance with the practice of the invention, merely by way of example, when the heparinoid is chondroitin sulfate, the amount of heparinoid in the composition may be about 1 mg to about 10,000 mg of chondroitin sulfate per unit dose (for example about 100 mg to about 300 mg per unit dose of chondroitin sulfate). In accordance with the practice of the invention, merely by way of example, when the heparinoid is heparin sodium, the amount of heparinoid in the composition may be about 10 mg to about 1000 mg of heparin sodium per unit dose.

The local anesthetic is typically a sodium channel blocker, such as, but not limited to, the drugs referred to commonly as the "caine" drugs, as well as other sodium channel blockers. The local anesthetic in a composition prepared according to the methods of the present invention can be, but is not limited to, any of benzocaine, lidocaine, tetracaine, bupivacaine, etidocaine, mepivacaine, pramoxine, prilocaine, procaine, chloroprocaine, oxyprocaine, proparacaine, ropivacaine, dyclonine, dibucaine, propoxycaine, dexivacaine, diamocaine, hexylcaine, levobupivacaine, pyrrocaine, risocaine, rodocaine, and pharmaceutically acceptable derivatives and bioisosteres thereof, or a combination thereof. Preferably, the anesthetic (e.g., the local anesthetic) is selected from the group consisting of lidocaine, bupivacaine, benzocaine, tetracaine, etidocaine, prilocaine, and dibucaine, or a combination thereof. A particularly preferred local anesthetic is lidocaine; preferably, the lidocaine is in the form of lidocaine hydrochloride, in which the chloride acts as a counterion. As used herein, the recitation of a local anesthetic includes all salts of that local anesthetic that are compatible with the desired pH, the buffer used, and any counterions present; the recitation of a local anesthetic is not intended to limit the salt form or counterion used beyond these criteria. Specifically, reference to an local anesthetic that possesses a positive charge at physiological or near-physiological pH, such as lidocaine, without specific reference to a counterion, is to be understood as including all possible counterions that do not interfere with the physiological activity of the lidocaine or other components of the composition and do not create incompatibility with any other components of the composition.

The quantity of local anesthetic in the composition will vary depending on the subject, the severity and course of the disease, the subject's health, the response to treatment, pharmacokinetic considerations such as liver and kidney function, and the judgment of the treating physician. Accordingly, a number of compositions including differing quantities of local anesthetic per unit dose can be prepared by methods according to the present invention. For example, when the local anesthetic is lidocaine, such as lidocaine hydrochloride, the amount of lidocaine in the composition may be in the range of about 10 mg to about 400 mg per unit dose, any intermediate quantity of lidocaine, such as 10 mg, 20 mg, 30 mg, 40 mg. 50 mg, 60 mg, 70 mg, 80 mg, 90 mg, 100 mg, 110 mg, 120 mg. 130 mg, 140 mg, 150 mg, 160 mg, 170 mg, 180 mg, 190 mg, 200 mg, 220 mg, 240 mg, 260 mg, 280 mg, 300 mg, 320 mg, 340 mg, 360 mg, 380 mg, or 400 mg per unit dose of the composition can be used. Typically, the concentration of the lidocaine of the composition included in the article of manufacture is from about 5 mg/mL to about 20 mg/mL. For example, the amount of lidocaine can be 10 mL of 1% lidocaine per unit dose or 16 mL of 2% lidocaine per unit dose. In one preferred embodiment, the composition comprises 200 mg of lidocaine as lidocaine hydrochloride. Suitable quantities of local anesthetics other than lidocaine can be determined by one of ordinary skill in the art based on the molecular weight and anesthetic potency of the local anesthetic to be used.

The buffer in a composition according to the present invention can be, but is not limited to, phosphate buffer, bicarbonate buffer, Tris (Tris(hydroxymethyl)aminomethane) buffer, MOPS buffer (3-(N-morpholino)propanesulfonic acid), HEPES (N-(2-hydroxyethyl)piperazine-N-(2-ethanesulfonic acid) buffer, ACES (2-[(2-amino-2-oxoethyl)amino]ethanesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1- propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS (N-(2-hydroxyethylpiperazine)-N'-(3-propanesulfonic acid) buffer, HEPPSO (N-(2-hydroxyethyl) piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, MOPSO (3-(N-morpholino)-2-hydroxy-propanesulfonic acid) buffer, PIPES (piperazine-N,N'-bis(2-ethanesulfonic acid) buffer, POPSO (piperazine-N,N'-bis(2-hydroxypropaneulfonic acid) buffer, TAPS (N-tris [hydroxymethyl)methyl-3-aminopropanesulfonic acid) buffer; TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, or a combination thereof. Particularly preferred buffers are bicarbonate buffer, phosphate buffer, Tris buffer or a combination thereof. A most particularly preferred buffer is phosphate buffer, particularly sodium phosphate buffer. Specific examples in which the buffer of the composition is phosphate buffer are described below. When the buffer is bicarbonate buffer, the bicarbonate buffer is preferably sodium bicarbonate.

Because phosphate can bind up to three hydrogen ions, it can exist in several forms, including dihydrogen phosphate ($H_2PO_4^-$), the monohydrogen phosphate ($HPO_4^{-2}$), and the phosphate ion itself ($PO_4^{3-}$). The $pK_a$ of the first ionization of phosphoric acid ($H_3PO_4$) to produce dihydrogen phosphate is about 2.12. The $pK_a$ of the ionization of dihydrogen phosphate to produce monohydrogen phosphate is about 7.21. The $pK_a$ of the ionization of monohydrogen phosphate to produce phosphate ion is about 12.67. The relative proportions of dihydrogen phosphate, monohydrogen phosphate, and phosphate ion present at a specified pH can readily be determined by use of the Henderson-Hasselbalch equation. Typically, when phosphate buffer is employed, it is employed as dihydrogen phosphate in view of the pH ranges involved; however, it is also possible to employ monohydrogen phosphate and add an alkalinizing agent such as sodium hydroxide to raise the pH to the desired value. Alternatively, a combination of monohydrogen phosphate and dihydrogen phosphate can be employed. Although it is possible to use other hydroxides such as potassium hydroxide, it is generally preferred to use sodium hydroxide in preference to potassium hydroxide in view of the potential role of potassium ion in the etiology of a number of lower urinary tract conditions. Phosphate buffer is a preferred buffer in some alternatives because it is more physiologically acceptable to the bladder and is normally present in urine.

In general, it is preferred to use an alkalinizing agent such as sodium hydroxide to achieve the final pH, rather than the buffer itself. The use of the alkalinizing agent to achieve the final pH results in greater stability of the acute-acting anesthetic, particularly lidocaine.

Other, optional, components, can be included in the composition. Such additional components can include:

(1) an osmolar component that provides an isotonic or nearly isotonic solution compatible with human cells and blood;

(2) a compound that enables persistence of the composition to the surface of the bladder epithelium in a quantity sufficient to treat, ameliorate, or prevent a lower urinary tract disorder;

(3) an antibacterial agent in a quantity sufficient to treat, ameliorate, or prevent a lower urinary tract disorder;

(4) an antifungal agent in a quantity sufficient to treat, ameliorate, or prevent a lower urinary tract disorder;

(5) a vasoconstrictor in a quantity sufficient to treat, ameliorate, or prevent a lower urinary tract disorder;

(6) a preservative; and (7) an anti-inflammatory agent.

When present, the optional osmolar component is a salt, such as sodium chloride, or a sugar or a combination of two or more of these components. The sugar may be a monosaccharide such as dextrose, a disaccharide such as sucrose or lactose, a polysaccharide such as dextran 40, dextran 60, or starch, or a sugar alcohol such as mannitol. It should be obvious to those skilled in the art that all components of the solution contribute to the osmolarity of the solution but to achieve an isotonic or near-isotonic solution, the contributions of those components should be taken into account to ensure that the proper proportion of osmolar component is added and an excess of osmolar component is not added which would result in a hypertonic solution. In fact, when the composition as described above includes heparin sodium as the heparinoid, lidocaine hydrochloride as the anesthetic, and sodium bicarbonate as the buffer, the osmolar contributions of the sodium ion from the heparin sodium and sodium bicarbonate, the chloride ion from the lidocaine hydrochloride, and the carbonate/bicarbonate ion from the sodium bicarbonate are sufficient not to require an additional osmolar component. Similarly, when phosphate buffer is used, the osmolar contributions of the sodium ion and the phosphate ion are typically sufficient not to require an additional osmolar component. However, in some alternatives, an additional osmolar component can be used.

If an antibacterial agent is present, the antibacterial agent can be selected from the group consisting of a sulfonamide, a penicillin, a combination of trimethoprim plus sulfamethoxazole, a quinolone, methenamine, nitrofurantoin, a cephalosporin, a carbapenem, an aminoglycoside, a tetracycline, a macrolide, and gentamicin. Suitable sulfonamides include, but are not limited to, sulfanilamide, sulfadiazine, sulfamethoxazole, sulfisoxazole, sulfamethizole, sulfadoxine, and sulfacetamide. Suitable penicillins include, but are not limited to, methicillin, nafcillin, oxacillin, cloxacillin, dicloxacillin, ampicillin, amoxicillin, bacampicillin, carbenicillin, ticarcillin, mezlocillin, and piperacillin. Suitable quinolones include, but are not limited to, nalidixic acid, levofloxacin, cinoxacin, norfloxacin, ciprofloxacin, orfloxacin, sparfloxacin, lomefloxacin, fleroxacin, pefloxacin, and amifloxacin. Suitable cephalosporins include, but are not limited to, cephalothin, cephazolin, cephalexin, cefadroxil, cefamandole, cefoxatin, cefaclor, cefuroxime, loracarbef, cefonicid, cefotetan, ceforanide, cefotaxime, cefpodoxime proxetil, ceftizoxime, ceftriaxone, cefoperazone, ceftazidime, and cefepime. Suitable carbepenems include, but are not limited to, imipenem, meropenem, and aztreonam. Suitable aminoglycosides include, but are not limited to, netilmycin and gentamicin. Suitable tetracyclines include, but are not limited to, tetracycline, oxytetracycline, demeclocycline, minocycline, doxycycline, and chlortetracycline. Suitable macrolides include, but are not limited to, erythromycin, clarithromycin, and azithromycin.

If an antifungal agent is present, the antifungal agent can be selected from the group consisting of amphotericin B, itraconazole, ketoconazole, fluconazole, miconazole, and flucytosine.

If a vasoconstrictor is present, the vasoconstrictor can be epinephrine.

If a compound that enables persistence of the composition to the surface of the bladder epithelium is present, the compound is typically an activatable gelling agent. The activatable gelling agent is typically a thermoreversible gelling agent. The thermoreversible gelling agent can be selected from the group consisting of Pluronics F127 gel, Lutrol gel, N-isopropylacrylamide, ethylmethacrylate, N-acryloxysuccinimide, xyloglucan sols of 1-2%, graft copolymers of pluronic and poly(acrylic acid), pluronic-chitosan hydrogels, and a [poly(ethylene glycol)-poly[lactic acid-co-glycolic acid]-poly(ethylene glycol)] (PEG-PLGA-PEG) copolymer.

If a preservative is present, the preservative can be selected from the group consisting of parabens, chlorobutanol, phenol, sorbic acid, and thimerosal. However, typically, compositions that form part of an article of manufacture according to the present invention do not require a preservative component and meet stability requirements without it. However, in some alternatives, it can be desirable to include a preservative component.

If an anti-inflammatory agent is present, the anti-inflammatory agent can be a steroid or a non-steroidal anti-inflammatory agent. Suitable steroids and non-steroidal anti-inflammatory agents are known in the art. Suitable steroids include, but are not limited to, hydrocortisone, cortisone, beclomethasone dipropionate, betamethasone, dexamethasone, prednisone, methylprednisolone, triamcinolone, fluocinolone acetonide, and fludrocortisone. Suitable non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac.

If any of these optional components, i.e., the osmolar component, the compound that enables persistence of the composition to the surface of the bladder epithelium, the antibacterial component, the antifungal compound, the vasoconstrictor, the preservative, or the anti-inflammatory agent, are present, they are typically added after a stable solution including the heparinoid, the acute-acting anesthetic, and the buffer has been prepared. The quantities of these additional optional components, if used, are chosen such that the solution of the heparinoid, the acute-acting anesthetic, and the buffer remains stable and precipitation of the acute-acting anesthetic is avoided and the final pH of the solution is achieved; the final pH is typically from about 6.8 to about 8.3 as described above. An optimum pH is about 7.3 to about 7.6, preferably about 7.5.

II. Methods of Preparing Compositions to be Incorporated in Article of Manufacture A number of methods of preparing compositions to be incorporated in an article of manufacture according to the present invention are described. These methods result in a composition that is then used to fill a syringe or vial, when the composition is packaged in a syringe or vial, which is the last step in preparation of the article of manufacture of the present invention. The alternatives for methods described below can be used to prepare the composition.

A first method comprises the steps of:

(1) providing a heparinoid, either as a solid or as an aqueous liquid, in a quantity of about 100 units to about 250,000 units per unit dose, or, alternatively, from about 0.5 mg to about 1250 mg per unit dose;

(2) providing a local anesthetic, either as a solid or as an aqueous liquid, in a quantity of from about 5 mg to about 1000 mg per unit dose;

(3) combining the heparinoid and the local anesthetic; and (4) buffering the combination of the heparinoid and the local anesthetic of step (3) to a pH value of greater than about 6.8 to about 8.3 with a buffer and the possible addition of a base selected from the group consisting of sodium hydroxide and potassium hydroxide compatible with both the heparinoid and the acute-acting anesthetic to form a stable solution.

Typically, as described above, the base used in step (4) is sodium hydroxide. Typically, the local anesthetic is lidocaine.

A second method comprises the steps of:

(1) providing a heparinoid, either as a solid or as an aqueous liquid, in a quantity of about 100 units to about 250,000 units per unit dose, or, alternatively, from about 0.5 mg to about 1250 mg per unit dose;

(2) buffering the heparinoid to a pH value of greater than about 6.8 to about 8.3 with a buffer compatible with both the heparinoid and a local anesthetic that is to be added subsequently;

(3) adding a local anesthetic, either as a solid or as an aqueous liquid, in a quantity of from about 5 mg to about 1000 mg per unit dose, to the buffered heparinoid from step (2) to form a solution including heparinoid, local anesthetic, and buffer; and (4) if required, rebuffering the solution of step (3) to a pH value of greater than about 6.8 to about 8.3 to form a stable solution.

Typically, the pH of the resulting solution is from about 7.3 to about 7.5.

In one particularly preferred method of preparing a composition according to the present invention, the composition is prepared by the following process:

(1) mixing the heparinoid and the acute-acting anesthetic to produce a liquid form in which the heparinoid and the acute-acting anesthetic are slightly more concentrated than in the final product;

(2) adding the buffer to produce a pH of about 7.0 to 7.3 in the solution of (1); and (3) raising the pH to a value in the range of from about 7.1 to about 8.3 using sodium hydroxide and adding water as required to achieve the final desired concentrations of the heparinoid and the acute-acting anesthetic.

In these alternatives, the heparinoid and the acute-acting anesthetic can be provided either in solid (e.g., powdered) form or in aqueous liquid form prior to the mixing process. All possible combinations of solid form and aqueous liquid form are possible for these processes; it is possible to use: (i) both the heparinoid and the acute-acting anesthetic in solid form; (ii) both the heparinoid and the acute-acting anesthetic in aqueous liquid form; (iii) the heparinoid in solid form, with the acute-acting anesthetic in aqueous liquid form; or (iv) the heparinoid in aqueous liquid form with the acute-acting anesthetic in solid form. However, as detailed below, when the heparinoid is heparin and the acute-acting anesthetic is lidocaine, it is necessary to employ powdered heparin and powdered lidocaine hydrochloride in the alternative processes described above, because available heparin and lidocaine hydrochloride solutions are not compatible upon the addition of buffer and the lidocaine precipitates regardless of subsequent attempts to avoid precipitation and maintain the lidocaine in solution. The resulting solution containing a heparinoid stabilizes the lidocaine at least partially as a free base; typically, from about 2% to about 45% of the lidocaine is present in the free base form.

The compositions described above that are included in an article of manufacture according to the present invention can be formulated for or are suitable for treating, ameliorating, or preventing a lower urinary tract disorder selected from the group consisting of bacterial cystitis, fungal/yeast cystitis, vulvar vestibulitis, vulvodynia, dyspareunia, urethral syndrome, and endometriosis in women; prostatitis and chronic pelvic pain syndrome in men; and radiation-induced cystitis, chemotherapy-induced cystitis, interstitial cystitis (also known as bladder pain syndrome (BPS) or hypersensitive bladder syndrome (HBS)), and overactive bladder in men or women. Compositions according to the present invention are particularly useful in treating interstitial cystitis.

As used herein, the terms "treat, ameliorate, or prevent" refer to any detectable improvement, whether subjective or objective, in the lower urinary tract disorder of the subject to whom the composition is administered. For example, the terms "treat, ameliorate, or prevent" can refer to an improvement as determined by the PORIS scale, the PUF scale, or any suitable assessment of those scales; reduction of pain; reduction of urinary frequency; reduction of urinary urgency; reduction of requirement for narcotic administration; reduction of incontinence; reduction of abnormal permeability of the urothelium to potassium; or improvement in more than one of these parameters. The terms "treat, ameliorate, or prevent" do not state or imply a cure for the underlying lower urinary tract disorder.

III. Glass and High Density Polyethylene, High Density Non-Nucleated Polypropylene, COP, or COC Plastics for Syringes and Vials An article of manufacture according to the present invention includes a syringe or vial constructed of either: (i) glass; or (ii) a plastic selected from the group consisting of COP (cyclic olefin polymer) plastic, COC (cyclic olefin copolymer) plastic, high density polyethylene plastic, and high density non-nucleated polypropylene plastic.

Cyclic olefin polymer plastics are disclosed in: U.S. Pat. No. 5,008,356 to Ishimaru et al.; U.S. Pat. No. 5,087,677 to Brekner et al.; U.S. Pat. No. 5,304,596 to Moriya et al.; U.S. Pat. No. 5,324,801 to Brekner et al.; U.S. Pat. No. 5,331,057 to Brekner et al.; U.S. Pat. No. 5,422,409 to Brekner et al.; U.S. Pat. No. 5,795,945 to Natori; U.S. Pat. No. 6,090,888 to Khananian et al.; U.S. Pat. No. 6,197,804 to Sunaga et al.; U.S. Pat. No. 6,388,032 to Yamaura et al.; U.S. Pat. No. 6,980,970 to Tsunogae et al.; U.S. Pat. No. 7,202,312 to Choi et al.; U.S. Pat. No. 7,648,937 to Yoon et al.; U.S. Pat. No. 7,814,713 to Yoon et al.; U.S. Pat. No. 7,838,088 to Suzuki et al.; U.S. Pat. No. 7,964,680 to Choi et al.; U.S. Pat. No. 7,989,570 to Chun et al.; U.S. Pat. No. 8,148,472 to Baugh et al.; U.S. Pat. No. 8,158,732 to Wakatsuki et al.; U.S. Pat. No. 8,293,674 to Chung et al.; U.S. Pat. No. 8,344,070 to Squire et al.; U.S. Pat. No. 8,883,925 to Kizu et al.; U.S. Pat. No. 8,946,366 to Yoo et al.; U.S. Pat. No. 9,056,938 to Sunaga et al.; U.S. Pat. No. 9,151,988 to Yoo et al.; U.S. Pat. No. 9,163,113 to Choi et al.; U.S. Pat. No. 9,206,278 to Yoshida et al.; and U.S. Pat. No. 9,359,588 to Smith.

Among the monomers that can be used to form cyclic olefin polymer plastics are norbornene; tetracyclododecene; bicyclo[2,2,1]hept-2-ene; 1-methylbicyclo[2,2,1]hept-2-ene; hexacyclo[6,6,1,1$^{3,6}$1$^{10,13}$,0$^{2,7}$, 0$^{9,14}$]-4-heptadecene; 1,4,5,8-dimethano-1,2,3,4,4a,5,8a-octahydronaphthalene; 2-methyl-1,4,5,8-dimethano-1,2,3,4,4a,5,8,8a-octahydronaphthalene; 2-ethyl-1,4,5,8-dimethano-1,2,3,4,4a,5,8,8a-octahydronaphthalene; 2-propyl-1,4,5,8-dimethano-1,2,3,4,4a,5,8,8a-octahydronaphthalene; 2-hexyl-1,4,5,8-dimethano-1,2,3,4,4a,5,8,8a-octahydronaphthalene; 2-stearyl-1,4,5,8-dimethano-1,2,3,4,4a,5,8,8a-octahydronaphthalene; 2,3-dimethyl-1,4,5,8-dimethano-1,2,3,4,4a,5,8,8a-octahydronaphthalene; 2-methyl-3-ethyl-1,4,5,8-dimethano-1,2,3,4,4a,5,8,8a-octahydronaphthalene; 2-chloro-1,4,5,8-dimethano-1,2,3,4,4a,5,8,8a-octahydronaphthalene; 2-bromo-1,4,5,8-dimethano-1,2,3,4,4a,5,8,8a-octahydronaphthalene; 2,3-dichloro-1,4,5,8-dimethano-1,2,3,4,4a,5,8,8a-octahydronaphthalene; 2-cyclohexyl-1,4,5,8-dimethano-1,2,3,4,4a,5,8,8a-octahydronaphthalene; 2-n-butyl-1,4,5,8-dimethano-1,2,3,4,4a,5,8,8a-octahydronaphthalene; 2-isobutyl-1,4,5,8-dimethano-1,2,3,4,4a,5,8,8a-octahydronaphthalene; bicyclo[2,2,1]hept-2-ene; 6-methylbicyclo[2,2,1]hept-2-ene; 5,6-dimethylbicyclo[2,2,1]hept-2-ene; 1-methylbicyclo[2,2,1]hept-2-ene; 6-ethylbicyclo[2,2,1]hept-2-ene; 6-n-butylbicyclo[2,2,1]hept-2-ene; 6-i-butylbicyclo[2,2,1]hept-2-ene; 7-methylbicyclo[2,2,1]hept-2-ene; 5,10-dimethyltetracyclo[4,4,0,1$^{2,5}$,1$^{7,10}$]3-dodecene; 2,10-dimethyltetracyclo[4,4,0,1$^{2,5}$,1$^{7,10}$]3 dodecene; 11,12-dimethyltetracyclo[4,4,0,1$^{2,5}$,1$^{7,10}$]3-dodecene; 2,7,9-trimethyltetracyclo[4,4,0,1$^{2,5}$,1$^{7,10}$]3-dodecene; 9-ethyl-2,7-dimethyl-tetracyclo[4,4,0,1$^{2,5}$1$^{7,10}$]3-dodecene; 9-isobutyl-2,7-dimethyl-tetracyclo[4,4,0,1$^{2,5}$1$^{7,10}$]3-dodecene; 9,11,12-trimethyl-tetracyclo[4,4,0,1$^{2,5}$1$^{7,10}$]3-dodecene; 9-ethyl-11,12-dimethyl-tetracyclo[4,4,0,1$^{2,5}$,1$^{7,10}$]3-dodecene; 9-isobutyl-11,12-dimethyl-tetracyclo[4,4,0,1$^{2,5}$,1$^{7,10}$]3-dodecene; 5,8,9-10-tetramethyl-tetracyclo[4,4,0,1$^{2,5}$,1$^{7,10}$]3-dodecene; hexacyclo[6,6,1,1$^{3,6}$,1$^{10,13}$ 0$^{2,7}$,0$^{9,14}$]4-heptadecene; 12-methylhexacyclo[6,6,1,1$^{3,6}$,1$^{10,13}$,0$^{2,7}$, 0$^{9,14}$]4-heptadecene; 12-ethylhexacyclo[6,6,1,1$^{3,6}$ 1$^{10,13}$,0$^{2,7}$,0$^{9,14}$]4-heptadecene; 12-isobutyl-hexacyclo[6,6,1,1$^{3,6}$,1$^{10,13}$,0$^{2,7}$, 0$^{9,14}$]4-heptadecene; 1,6,10-trimethyl-12-isobutyl-hexacyclo[6,6,1,1$^{3,6}$,1$^{10,13}$,0$^{2,7}$,0$^{9,14}$]4-heptadecene; octacyclo-[8,8,1$^{2,9}$1$^{4,7}$1$^{11,18}$, 1$^{13,16}$ 0,0$^{3,8}$, 0$^{12,17}$]-5-dococene; 15-methyl-octacyclo-[8,8,1$^{2,9}$,1$^{4,7}$, 1$^{11,18}$,1$^{13,16}$, 0,0$^{3,8}$, 0$^{12,17}$]-5-dococene; 15-ethyl-octacyclo-[8,8,1$^{2,9}$,1$^{4,7}$, 1$^{11,18}$, 1$^{13,16}$ 0,0$^{3,8}$, 0$^{12,17}$]-5-dococene; tricyclo[4,3,0,1$^{2,5}$]-decene;

2-methyltricyclo[4,3,0,1$^{2,5}$]-decene; 5-methyltricyclo[4,3,0, 1$^{2,5}$]-decene; tricyclo[4,4,0,1$^{2,5}$]-decene; 10-methyltricyclo[4,4,0,1$^{2,5}$]-decene; 1,3-dimethylpentacyclo-[6,6,1,1$^{3,6}$,0$^{2,7}$, 0$^{9,14}$]4-hexadecene; 1,6-dimethylpentacyclo-[6,6,1,1$^{3,6}$, 0$^{2,7}$,0$^{9,14}$]4 hexadecene; 15,16-dimethylpentacyclo-[6,6,1, 1$^{3,6}$,0$^{2,7}$,0$^{9,14}$]4-hexadecene; pentacyclo[6,5,1,1$^{3,6}$,0$^{2,7}$, 0$^{9,13}$]-4-pentadecene; 1,3-dimethylpentacyclo[6,5,1,1$^{3,6}$, 0$^{2,7}$,0$^{9,13}$]-4-pentadecene, 1,6-dimethylpentacyclo[6,5, 1,1$^{3,6}$,0$^{2,7}$,0$^{9,13}$]-4-pentadecene; 14,15-dimethylpentacyclo [6,5,1,1$^{3,6}$,0$^{2,7}$, 0$^{9,13}$]-4-pentadecene; pentacyclo[6,6,1,1$^{3,6}$, 0$^{2,7}$,0$^{9,14}$]-4-hexadecene; heptacyclo[8,7,1$^{2,9}$,1$^{4,7}$, 1$^{11,17}$, 0,0$^{3,8}$,0$^{12,16}$]-5-eicosene; and pentacyclo[8,8,1$^{2,9}$1$^{4,7}$,1$^{11,18}$, 0,0$^{3,8}$,0$^{12,17}$]. Other suitable monomers are known in the art.

Suitable catalysts for polymerization for the formation of cyclic olefin polymer plastics are known in the art and include, but are not limited to: catalysts comprising transition metal compounds and aluminoxanes; titanium-containing catalysts comprising titanium compounds and organoaluminum compounds; vanadium-containing catalysts comprising vanadium compounds and organoaluminum compounds; and other catalysts. In one alternative, the transition metal compound is a zirconium compound. Suitable zirconium compounds include, but are not limited to: ethylenebis(indenyl)zirconium dichloride; ethylenebis(indenyl)zirconium monochloride monohydride; ethylenebis(indenyl)ethoxyzirconium chloride; ethylenebis(4,5,6,7-tetrahydro-1-indenyl)ethoxyzirconium chloride; ethylenebis (indenyl)dimethylzirconium; ethylenebis(indenyl) diethylzirconium; ethylenebis(indenyl)diphenylzirconium; ethylenebis(indenyl)dibenzylzirconium; ethylenebis(indenyl)methylzirconium monobromide; ethylenebis(indenyl) ethylzirconium monochloride; ethylenebis(indenyl)benzylzirconium monochloride; ethylenebis(indenyl) methylzirconium monochloride; ethylenebis(indenyl) zirconium dichloride; ethylenebis(indenyl)zirconium dibromide; ethylenebis(4,5,6,7-tetrahydro-1-indenyl)dimethylzirconium; ethylenebis(4,5,6,7-tetrahydro-1-indenyl) ethylzirconium ethoxide; ethylenebis(4,5,6,7-tetrahydro-1-indenyl)zirconium dichloride; ethylenebis(4,5,6,7-tetrahydro-1-indenyl)zirconium dibromide, ethylenebis(4-methyl-1-indenyl)zirconium dichloride; ethylenebis(5-methyl-1-indenyl)zirconium dichloride; ethylenebis(6-methyl-1-indenyl)zirconium dichloride; ethylenebis(7-methyl-1-indenyl)zirconium dichloride; ethylenebis(5-methoxy-1-indenyl)zirconium dichloride; ethylenebis(2,3-dimethyl-1-indenyl)zirconium dichloride; ethylenebis(4,7-dimethyl-1-indenyl)zirconium dichloride; ethylenebis(4,7-dimethoxy-1-indenyl)zirconium dichloride; ethylenebis (indenyl)zirconium dimethoxide; ethylenebis(indenyl) zirconium diethoxide; ethylenebis(indenyl) methoxyzirconium chloride; ethylenebis(indenyl) ethoxyzirconium chloride; ethylenebis(indenyl) methylzirconium ethoxide; ethylenebis(4,5,6,7-tetrahydro-1-indenyl)zirconium dimethoxide; ethylenebis(4,5,6,7-tetrahydro-1-indenyl)zirconium diethoxide; ethylenebis(4,5, 6,7-tetrahydro-1-indenyl)methoxyzirconium chloride; ethylenebis(4,5,6,7-tetrahydro-1-indenyl)methylenebis(indenyl)methylzirconium ethoxide, methylenebis(indenyl)zirconium dichloride; methylenebis(indenyl)dimethylzirconium; methylenebis(4,5,6,7-tetrahydro-1-indenyl)zirconium dichloride; propylenebis(indenyl)zirconium dichloride; propylenebis(indenyl)dimethylzirconium, and propylenebis(4, 5,6,7-tetrahydro-1-indenyl)zirconium dichloride.

The aluminoxane component of the catalyst can be, but is not limited to, an organoaluminum compound of Formula (C-1) or Formula (C-II):

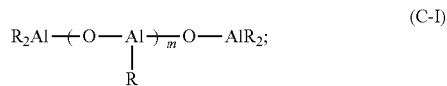

(C-I)

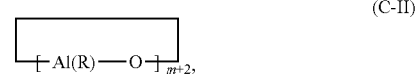

(C-II)

wherein: R is a hydrocarbon group such as a methyl, ethyl, n-propyl, isopropyl, n-butyl, or isobutyl group, preferably, methyl, ethyl, or isobutyl, more preferably methyl; and m is an integer of 2 or more, preferably 5 or more.

Other catalysts and components for catalysts for polymerization of cyclic olefin polymers are known in the art.

Syringes constructed from a cyclic olefin polymer are described in U.S. Pat. No. 9,381,687 to Felts et al.; U.S. Pat. No. 9,220,631 to Sigg et al.; U.S. Pat. No. 8,939,940 to Haury et al.; U.S. Pat. No. 8,747,726 to Haury et al.; U.S. Pat. No. 8,721,603 to Lundquist; U.S. Pat. No. 8,679,068 to Young; U.S. Pat. No. 8,398,600 to Hirokane et al.; U.S. Pat. No. 8,303,540 to Shue et al.; U.S. Pat. No. 7,766,882 to Sudo et al.; and U.S. Pat. No. 7,740,792 to Haury et al. The barrel of the syringe can be injection molded or formed by other techniques known in the art.

Cyclic olefin copolymer plastics are described in U.S. Pat. No. 5,559,199 to Abe et al.; U.S. Pat. No. 6,627,714 to Yamamoto et al.; U.S. Pat. No. 6,639,021 to Oshima et al.; U.S. Pat. No. 6,844,403 to Oshima et al.; U.S. Pat. No. 6,992,154 to Oshima et al.; U.S. Pat. No. 7,122,239 to Bennett et al.; U.S. Pat. No. 7,258,930 to Rivett et al.; U.S. Pat. No. 7,468,417 to Jang et al.; U.S. Pat. No. 7,662,445 to Nagura et al.; U.S. Pat. No. 7,854,873 to Heidari et al.; U.S. Pat. No. 8,084,563 to Sakagami et al.; U.S. Pat. No. 8,541, 621 to Shin et al.; U.S. Pat. No. 8,637,128 to Jemelin; U.S. Pat. No. 9,206,278 to Yoshida et al.; and U.S. Pat. No. 9,359,558 to Smith.

Cyclic olefins suitable as comonomers in the cyclic olefin copolymers are known in the art, including the cyclic olefins described above. Other olefins useful as comonomers are known in the art, and include ethylene and other linear olefins having from 3 to 20 carbon atoms, such as propylene, 1-butene, 1-hexene, 4-methyl-1-pentene, 1-octane, 1-decene, 1-dodecene, 1-tetradecene, 1-hexadecene, 1-octadecene, and 1-eicosene.

Suitable catalysts for production of these copolymers are described above with respect to the production of cyclic olefin polymers. Other catalysts are known in the art, and include zirconium compounds, nickel compounds, cobalt compounds, palladium compounds, platinum compounds, rhenium compounds, and ruthenium compounds, and complexes of a tungsten salt and an organoaluminum halide compound. Additional catalysts are described in U.S. Pat. No. 5,559,199 to Abe et al.; U.S. Pat. No. 6,639,021 to Oshima et al.; U.S. Pat. No. 6,844,403 to Oshima et al.; U.S. Pat. No. 7,468,417 to Jang et al.; and U.S. Pat. No. 8,084,563 to Sakagami et al.

Syringes constructed from a cyclic olefin copolymer are described in U.S. Pat. No. 9,381,687 to Felts et al.; U.S. Pat. No. 8,721,603 to Lundquist; U.S. Pat. No. 8,679,068 to Young; U.S. Pat. No. 7,041,087 to Henderson et al.; and U.S. Pat. No. 6,065,270 to Reinhard et al.

High density polyethylene typically has a density of from 0.93 g/cm$^3$ to 0.97 g/cm$^3$. High density polyethylene has little branching, which is assured by an appropriate choice of catalyst, such as Ziegler-Natta catalyst, and reaction conditions. Syringes constructed of high density polyethylene are disclosed in U.S. Pat. No. 9,533,103 to Okihara; U.S. Pat. No. 9,381,687 to Felts et al.; and U.S. Pat. No. 9,302,050 to Creaturo et al.

High density polypropylene typically has a density of from 0.895 g/cm$^3$ to 0.92 g/cm$^3$. Such polypropylene can be produced using metallocene catalysis. A particularly useful form of polypropylene is non-nucleated polypropylene, such as Eltex® MED 100-MG03 (INEOS Olefins and Polymers). Syringes constructed of high density polypropylene are disclosed in U.S. Pat. No. 5,820,605 to Zdeb et al.

If sterilization of the composition prior to the filling of the syringe with the composition is required, it is typically performed by heat sterilization or steam sterilization, which is generally preferred by the FDA and EMA. One suitable method of terminal sterilization is sterilization by autoclaving, which is known in the art. Other sterilization methods, including sterilization by filtration, are known in the art, and can be alternatively used. In another alternative, the syringes can be sterilized separately and then filled aseptically with the solution. The final product can be produced by terminal sterilization or aseptically. Terminal sterilization is generally preferred.

A particularly preferred syringe is a syringe of 20-mL volume constructed of glass or plastic polymer as described above.

In one alternative, the interior of the syringe barrel is coated to reduce deposition of the local anesthetic on the syringe surface. A preferred coating is a siloxane coating deposited by a plasma deposition process such as that disclosed in U.S. Pat. No. 7,985,188 to Felts et al. and U.S. Pat. No. 8,627,970 to Macy et al.

One alternative for a preferred composition is prepared as follows in purified water:

(1) 16.67 g/L of heparin sodium;
(2) 13.33 g/L of lidocaine hydrochloride;
(3) 10.03 g/L of $Na_2HPO_4.12H_2O$ to produce a concentration of 0.028 M; and
(4) 0.02 N NaOH as needed to adjust pH.

Variations of this particularly preferred composition can also be prepared and are within the scope of the invention. For example, the quantity of heparin can be 16 g/L or another quantity. The lidocaine quantity can also be varied. If the heparinoid were a heparinoid other than heparin, the quantity of the heparinoid also could be varied. Similarly, if the local anesthetic were other than lidocaine, the quantity of the local anesthetic also could be varied.

This composition can then be loaded into the syringe or vial constructed of glass or plastic as described above.

The invention is illustrated by the following Examples. These Examples are included for illustrative purposes only, and are not intended to limit the invention.

Example 1

Comparative Example

Example 1 shows the stability of a solution containing 200 mg of lidocaine, 50,000 USP units of heparin, and phosphate buffer when stored in glass vials with a stopper and overseal.

Table 1 shows the stability of the solution containing 200 mg of lidocaine, 50,000 USP units of heparin, and phosphate buffer when stored in glass vials for 12 months at 5° C.±3° C. at ambient relative humidity with the glass vials upright.

TABLE 1

| Test & Method | Specifications | Initial[1] | One[2] | Three[3] | Six[4] | Twelve[5] |
|---|---|---|---|---|---|---|
| Appearance/ Visual | Clear, colorless to slightly yellow solution in clear glass vial with stopper and over seal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact |
| Heparin Anti-Factor IIa | 90.0%-110.0% of label claim | 106% | 99.0% | 98.6% | 87.4% | 99.6% |
| Heparin Anti-Factor Xa/IIa ratio | Anti-Factor Xa/Anti-Factor IIa ratio: 0.9-1.1 | 0.95 | 1.1 | 1.0 | 1.1 | 1.0 |
| Lidocaine Assay/ UR-AN-001-R0 | 90.0%-110.0% of label claim | 101% | 99.0% | 100.2% | 100.0% | 100.1% |
| Lidocaine RS/ UR-AN-002-R0 | Single largest impurity: NMT 0.2 % Total impurities: NMT 0.5% | No impurities detected (LOD: 0.03%) | No impurities detected (LOD: 0.03%) | No impurities detected (LOD: 0.03%) | Impurity testing not performed at this time point. Client Notified | No impurities detected (LOD: 0.03%) |
| pH/USP <791> | 7.4 ± 0.3 | 7.4 | 7.4 | 7.4 | 7.3 | 7.4 |

Table 2 shows the stability of the solution containing 200 mg of lidocaine, 50,000 USP units of heparin, and phosphate buffer when stored in glass vials for 12 months at 25° C.±2° C. at relative humidity of 60%±5% with the glass vials upright.

TABLE 2

| Test & Method | Specifications | Initial[1] | One[2] | Three[3] | Six[4] | Twelve[5] |
|---|---|---|---|---|---|---|
| Appearance/ Visual | Clear, colorless to slightly yellow solution in clear | Clear, colorless solution in clear glass vial with | Clear, colorless solution in clear glass vial with | Clear, colorless solution in clear glass vial with | Clear, colorless solution in clear glass vial with | Clear, colorless solution in clear glass vial with |

Table 3 shows the stability of the solution containing 200 mg of lidocaine, 50,000 USP units of heparin, and phosphate buffer when stored in glass vials for 12 months at 40° C.±2° C. at relative humidity of 60%±5% with the glass vials upright.

TABLE 2-continued

| Test & Method | Specifications | Initial[1] | One[2] | Three[3] | Six[4] | Twelve[5] |
|---|---|---|---|---|---|---|
| | glass vial with stopper and over seal intact | stopper and overseal intact | stopper and overseal intact | stopper and overseal intact | stopper and overseal intact | stopper and overseal intact |
| Heparin Anti-Factor IIa | 90.0%-110.0% of label claim | 106% | 116.0% | 106.6% | 93.0% | 103.7% |
| Heparin Anti-Factor Xa/IIa ratio | Anti-Factor Xa/Anti-Factor IIa ratio: 0.9-1.1 | 0.95 | 1.0 | 0.9 | 1.1 | 1.0 |
| Lidocaine Assay/ UR-AN-001-R0 | 90.0%-110.0% of label claim | 101% | 98.7% | 99.7% | 100.4% | 100.5% |
| Lidocaine RS/ UR-AN-002-R0 | Single largest impurity: NMT 0.2 % Total impurities: NMT 0.5% | No impurities detected (LOD: 0.03%) | No impurities detected (LOD: 0.03%) | No impurities detected (LOD: 0.03%) | Impurity testing not performed at this time point. Client Notified | No impurities detected (LOD: 0.03%) |
| pH/USP <791> | 7.4 ± 0.3 | 7.4 | 7.4 | 7.4 | 7.3 | 7.4 |
| Sterility/USP <71> | No Growth of Organisms | No growth observed | No growth observed | N/A | N/A | N/A |

TABLE 3

| Test & Method | Specifications | Initial[1] | One[2] | Three[3] | Six[4] | Twelve[5] |
|---|---|---|---|---|---|---|
| Appearance/ Visual | Clear, colorless to slightly yellow solution in clear glass vial with stopper and over seal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact |
| Heparin Anti-Factor IIa | 90.0%-110.0% of label claim | 106% | 100.9% | 98.5% | 98.0% | 102.1% |
| Heparin Anti-Factor Xa/IIa ratio | Anti-Factor Xa/Anti-Factor IIa ratio: 0.9-1.1 | 0.95 | 1.0 | 1.0 | 1.0 | 1.0 |
| Lidocaine Assay/ UR-AN-001-R0 | 90.0%-110.0% of label claim | 101% | 99.0% | 99.9% | 99.4% | 99.7% |
| Lidocaine RS/ UR-AN-002-R0 | Single largest impurity: NMT 0.2 % Total impurities: NMT 0.5% | No impurities detected (LOD: 0.03%) | No impurities detected (LOD: 0.03%) | No impurities detected (LOD: 0.03%) | Impurity testing not performed at this time point. Client Notified | No impurities detected (LOD: 0.03%) |
| pH/USP <791> | 7.4 ± 0.3 | 7.4 | 7.4 | 7.4 | 7.4 | 7.4 |

In all three cases (the data shown in Table 1, Table 2, and Table 3), the solutions were stable, with the heparin and lidocaine assays showing virtually no change from their initial values, no impurities being detected, and, where tests for growth of organisms were performed, no growth of organisms being detected.

Example 2

Stability of Compositions Comprising Heparin, Lidocaine, and Phosphate Buffer in Cyclic Olefin Polymer Syringes and Polypropylene Syringes and in Glass A composition comprising:
(1) 1.6 g of heparin sodium;
(2) 1.42 g of lidocaine hydrochloride;
(3) 1.003 g of $Na_2HPO_4 \cdot 12H_2O$;
(4) 1.0 mL of 2 N NaOH; and
(5) purified water to a total volume of 100 mL;
was used for these studies. This composition comprises:
(1) 16 g/L of heparin sodium;
(2) 14.2 g/L of lidocaine hydrochloride;
(3) 10.03 g/L of $Na_2HPO_4 \cdot 12H_2O$ to produce a concentration of 0.028 M; and
(4) 0.02 N NaOH as needed to adjust pH.

This composition was packaged in 20-mL cyclic olefin polymer (COP) and polypropylene (PP) syringes; the polypropylene was not non-nucleated. Storage conditions were, as indicated below, either 25° C./60% relative humidity (RH) or 40° C./75% RH.

Testing points were as follows: at the initiation of the stability study, after 1 month, 2 months, 3 months, 6 months, and 12 months.

Testing parameters were as follows: appearance, pH value, assay for heparin sodium, assay for lidocaine hydrochloride, and assay of DMA (2,6-dimethylaniline) and other impurities.

Table 4 shows the results for heparin sodium assay after 3 months.

TABLE 4

| Sample | | U/mg | | Anti Xa/IIa Ratio |
|---|---|---|---|---|
| | | Anti-Xa | Anti-IIa | |
| URG101 | PP syringes-25° C./60% RH, 3 months | 195.7 ± 0.3 | 203.0 ± 1.8 | 0.96 |
| URG101 | PP syringes-40° C./75% RH, 3 months | 221.4 ± 2.9 | 222.6 ± 3.1 | 0.99 |
| URG101 | COP syringes-25° C./60% RH, 3 months | 196.4 ± 1.3 | 197.9 ± 2.3 | 0.99 |
| URG101 | COP syringes-40° C./75% RH, 3 months | 204.9 ± 1.0 | 227.7 ± 2.4 | 0.90 |

| Sample | | U/mL | |
|---|---|---|---|
| | | Anti-Xa | Anti-IIa |
| URG101 | PP syringes-25° C./60% RH, 3 months | 2610.0 ± 3.9 | 2707 ± 23.4 |
| URG101 | PP syringes-40° C./75% RH, 3 months | 2951.4 ± 38.9 | 2968.1 ± 41.5 |
| URG101 | COP syringes-25° C./60% RH, 3 months | 2618.3 ± 17.1 | 2638.4 ± 30.8 |
| URG101 | COP syringes-40° C./75% RH, 3 months | 2732.1 ± 12.9 | 3036.3 ± 32.0 |

Table 5 shows more detailed results for sterility, appearance, pH value, assay of lidocaine, assay of DMA (2,6-dimethylaniline), and overall impurities at the start (before and after sterilization), 1 month, 2 months, 3 months, 6 months, and 12 months for storage conditions at 25° C.±2° C. and 60%±5% relative humidity for compositions stored in COP syringes.

Table 6 shows more detailed results for sterility, appearance, pH value, assay of lidocaine, assay of DMA (2,6-dimethylaniline), and overall impurities at the start (before and after sterilization), 1 month, 2 months, 3 months, 6 months, and 12 months for storage conditions at 40° C.±2° C. and 75%±5% relative humidity for compositions stored in COP syringes.

TABLE 5

Product: URG101 Batch-size: 600 g Manufacturer: Lena Blumer Date of manufacture: 5/5/2015
Container Closure System: 20 mL COP syringes Storage conditions: 25° ± 2° C./60% ± 5% RH

| Test | Specification | Start unsterile | Start sterile | 1 month | 2 months | 3 months | 6 months | 12 months |
|---|---|---|---|---|---|---|---|---|
| Appearance manufactured good | 20 mL syringes made of cyclo olefin polymer with grey plunger and tip caps | compliance | compliance | compliance | compliance | compliance | compliance | compliance |
| Apperance filled (sterile) good | colourless clear solution | compliance | compliance | compliance | compliance | compliance | compliance | compliance |
| Activity Heparin sodium | | | | | | | | |
| Anti-Xa [U/ml] | | — | — | — | — | 2618.3 ± 17.1 | — | — |
| Anti-IIa [U/ml] | | — | — | — | — | 2638.4 ± 30.8 | — | — |
| pH value | 7.4 +/− 0.2 | 7.46 | 7.42 | 7.38 | 7.44 | 7.41 | 7.41 | 7.44 |
| Assay lidocaine HCl [g/100 g] | 1.26-1.40 g/ 100 g | 1.34 | 1.34 | 1.33 | 1.33 | 1.33 | 1.34 | 1.35 |
| Loss of lidocaine HCl | | — | 0.00% | 0.75% | 0.75% | 0.75% | 0.00% | −0.75% |
| Assay DMA [ppm] | max. 8 ppm | 0.00 | 0.56 | 0.67 | 0.54 | 0.51 | 0.63 | 1.07 |
| Impurity B | | 0.000 | 0.016 | 0.012 | 0.007 | 0.009 | 0.024 | 0.053 |
| Impurity 4 | | | | | | | | 0.013 |
| Impurity 5 | | 0.000 | 0.014 | 0.012 | 0.021 | 0.019 | 0.028 | |
| Impurity H | | | | | | | | |
| Impurity 6 | | | | | | | | |
| Impurity 7 | | | | | | | | 0.041 |
| Impurity 8 | | | | | | | | |
| Impurity 9 | | | | | | | | |
| Sum Impurities | max. 0.75 | 0.000 | 0.030 | 0.024 | 0.028 | 0.029 | 0.053 | 0.107 |

TABLE 6

Storage Conditions 40° C. ± 2° C./75% ± 5% RH

| Test | Specification | Start unsterile | Start sterile | 1 month | 2 months | 3 months | 6 months | 12 months |
|---|---|---|---|---|---|---|---|---|
| Appearance manufactured good | 20 mL syringes made of cyclo olefin polymer with grey plunger and tip caps | compliance | compliance | compliance | compliance | compliance | compliance | compliance |
| Appearance filled (sterile) good | colorless clear solution | compliance | compliance | compliance | compliance | compliance | compliance | compliance |
| Activity Heparin sodium | | | | | | | | |
| Anti-Xa [U/ml] | | — | — | — | — | 2732.1 ± 12.9 | — | — |
| Anti-IIa [U/ml] | | — | — | — | — | 3036.3 ± 32.0 | — | — |
| pH value | 7.4 +/− 0.2 | 7.46 | 7.42 | 7.37 | 7.39 | 7.39 | 7.36 | 7.37 |
| Assay lidocaine HCl [g/100 g] | 1.26-1.40 g/ 100 g | 1.34 | 1.34 | 1.33 | 1.31 | 1.30 | 1.29 | 1.29 |
| Loss of lidocaine HCl | | — | 0.00% | 0.75% | 2.24% | 2.99% | 3.73% | 3.73% |
| Assay DMA [ppm] | max. 8 ppm | 0.00 | 0.56 | 0.72 | 0.82 | 1.00 | 1.41 | 2.28 |
| Impurity B | | 0.000 | 0.016 | 0.028 | 0.046 | 0.057 | 0.115 | 0.183 |
| Impurity 4 | | | | | | | | 0.013 |
| Impurity 5 | | 0.000 | 0.014 | 0.028 | 0.043 | 0.048 | 0.079 | 0.018 |
| Impurity H | | | | | | | | 0.019 |
| Impurity 6 | | | | | | | | 0.033 |
| Impurity 7 | | | | | | | | 0.106 |
| Impurity 8 | | | | | | | | 0.014 |
| Impurity 9 | | | | | | | | 0.050 |
| Sum Impurities | max. 0.75 | 0.000 | 0.030 | 0.056 | 0.089 | 0.105 | 0.194 | 0.439 |

Table 7 shows more detailed results for sterility, appearance, pH value, assay of lidocaine, assay of DMA, and overall impurities at the start (before and after sterilization), 1 month, 2 months, 3 months, 6 months, and 12 months for storage conditions at 25° C.±2° C. and 60%±5% relative humidity for compositions stored in PP syringes; the polypropylene was not non-nucleated.

TABLE 7

| Test | Specification | Start unsterile | Start sterile | 1 month | 2 months | 3 months | 6 months | 12 months |
|---|---|---|---|---|---|---|---|---|
| Appearance manufactured good | 20 mL syringes made of polypropylene with blue plunger and tip caps | compliance | compliance | compliance | compliance | compliance | compliance | compliance |
| Appearance filled (sterile) good | colorless clear solution | compliance | compliance | compliance | compliance | compliance | compliance | compliance |
| Activity Heparin sodium | | | | | | | | |
| Anti-Xa [U/ml] | | — | — | — | — | 2610.0 ± 3.9 | — | 2615.64 |
| Anti-IIa [U/ml] | | — | — | — | — | 2707 ± 23.4 | — | 2620.21 |
| pH value | 7.4 +/− 0.2 | 7.46 | 7.3 | 7.26 | 7.26 | 7.28 | 7.26 | 7.27 |
| Assay lidocaine HCl [g/100 g] | 1.26-1.40 g/ 100 g | 1.34 | 1.23 | 1.22 | 1.21 | 1.21 | 1.22 | 1.23 |

TABLE 7-continued

| Test | Specification | Start unsterile | Start sterile | 1 month | 2 months | 3 months | 6 months | 12 months |
|---|---|---|---|---|---|---|---|---|
| Loss of lidocaine HCl | — | | 8.21% | 8.96% | 9.70% | 9.70% | 8.96% | 8.21% |
| Assay DMA [ppm] | max. 8 ppm | 0.00 | 0.52 | 0.33 | 0.44 | 0.34 | 0.40 | 0.68 |
| Impurity B | | 0.000 | 0.017 | 0.015 | 0.014 | 0.008 | 0.021 | 0.049 |
| Impurity 4 | | | | | | | | 0.009 |
| Impurity 5 | | 0.000 | 0.018 | 0.015 | 0.017 | 0.017 | 0.023 | |
| Impurity H | | | | | | | | |
| Impurity 6 | | | | | | | | |
| Impurity 7 | | | | | | | | 0.040 |
| Impurity 8 | | | | | | | | |
| Impurity 9 | | | | | | | | |
| Sum Impurities | max. 0.75 | 0.000 | 0.035 | 0.030 | 0.031 | 0.026 | 0.044 | 0.098 |

Table 8 shows more detailed results for sterility, appearance, pH value, assay of lidocaine, assay of DMA, and overall impurities at the start (before and after sterilization), 1 month, 2 months, 3 months, 6 months, and 12 months for storage conditions at 40° C.±2° C. and 75%±5% relative humidity for compositions stored in PP syringes; the polypropylene was not non-nucleated.

TABLE 8

Product: URG101 Batch-size: 600 g Manufacturer: Lena Blumer Date of manufacture: 5/5/2015
Container Closure System: 20 mL PP syringes Storage conditions: 40° ± 2° C./75% ± 5% RH

| Test | Specification | Start unsterile | Start sterile | 1 month | 2 months | 3 months | 6 months | 12 months |
|---|---|---|---|---|---|---|---|---|
| Appearance manufactured good | 20 mL syringes made of polypropylene with blue plunger and tip caps | compliance | compliance | compliance | compliance | compliance | compliance | compliance |
| Appearance filled (sterile) good | colorless clear solution | compliance | compliance | compliance | compliance | compliance | compliance | compliance |
| Activity Heparin sodium | | | | | | | | |
| Anti-Xa [U/ml] | | — | — | — | — | 2951.4 ± 38.9 | — | 2853.64 |
| Anti-IIa [U/ml] | | — | — | — | — | 2968.1 ± 41.5 | — | 2862.21 |
| pH value | 7.4 +/− 0.2 | 7.46 | 7.30 | 7.25 | 7.24 | 7.23 | 7.17 | 7.15 |
| Assay lidocaine HCl [g/100 g] | 1.26-1.40 g/100 g | 1.34 | 1.23 | 1.22 | 1.18 | 1.20 | 1.16 | 1.15 |
| Loss of lidocaine HCl | — | | 8.21% | 8.96% | 11.94% | 10.45% | 13.43% | 14.18% |
| Assay DMA [ppm] | max. 8 ppm | 0.00 | 0.52 | 0.42 | 0.58 | 0.61 | 0.94 | 1.51 |
| Impurity B | | 0.000 | 0.017 | 0.027 | 0.040 | 0.049 | 0.103 | 0.226 |
| Impurity 4 | | | | | | | | 0.018 |
| Impurity 5 | | 0.000 | 0.018 | 0.029 | 0.040 | 0.052 | 0.080 | 0.008 |
| Impurity H | | | | | | | | 0.014 |
| Impurity 6 | | | | | | | | 0.027 |
| Impurity 7 | | | | | | | | 0.124 |
| Impurity 8 | | | | | | | | 0.008 |
| Impurity 9 | | | | | | | | 0.041 |
| Sum Impurities | max. 0.75 | 0.000 | 0.035 | 0.055 | 0.080 | 0.101 | 0.183 | 0.466 |

FIG. 1 shows the results for stability of pH values in COP syringes (left panel) and PP syringes (right panel) at 25° C./60% RH and at 40° C./75% RH for up to 6 months; the polypropylene was not non-nucleated.

The pH value is stable in COP syringes in stability storage tests. The pH value complies with the specification of from 7.2 to 7.6 at the testing points. However, for storage in PP syringes, the pH value decreases after sterilization in PP syringes (the polypropylene was not non-nucleated). Although the pH value complies with the specification at 25° C./60% RH, it is out of the specification at 40° C./75% RH after 6 months.

Figure 2:
FIG. 2 shows the results for stability of lidocaine concentration in COP syringes (left panel) and PP syringes (right panel) in Example 2 for up to 6 months.

FIG. 2 shows the results for stability of lidocaine concentration in COP syringes (left panel) and PP syringes (right panel) at 25° C./60% RH and at 40° C./75% RH for up to 6 months; the polypropylene was not non-nucleated.

The assay of lidocaine concentration is stable in COP syringes in stability storage tests and complies with the specification of 1.26-1.40 g/100 g at all testing points. However, for PP syringes, the lidocaine assay decreases after sterilization but is stable on further storage; the lidocaine assay does continue to decrease under accelerated conditions such as high temperature. All time points after sterilization are out of compliance with the specification for PP syringes (the polypropylene was not non-nucleated).

For impurities, 2,6-dimethylaniline and other impurities increase slightly in the course of stability storage tests, with a stronger increase at 40° C./75% RH than for 25° C./60% RH. However, the same impurity profiles and similar amounts of the impurities occur in both COP and PP syringes, and the impurities are independent of the loss of lidocaine. However, the impurity level is lower than the threshold in both COP and PP in both storage conditions and at all testing points.

FIG. 3 shows the results of stability storage tests at 25° C./60% RH in COP syringes.

FIG. 4 shows the results of stability storage tests at 40° C./75% RH in COP syringes.

FIG. 5 shows the results of stability storage tests at 25° C./60% RH in PP syringes; the polypropylene syringes were not non-nucleated.

FIG. 6 shows the results of stability storage tests at 40° C./75% RH in PP syringes; the polypropylene syringes were not non-nucleated.

Figure 7:
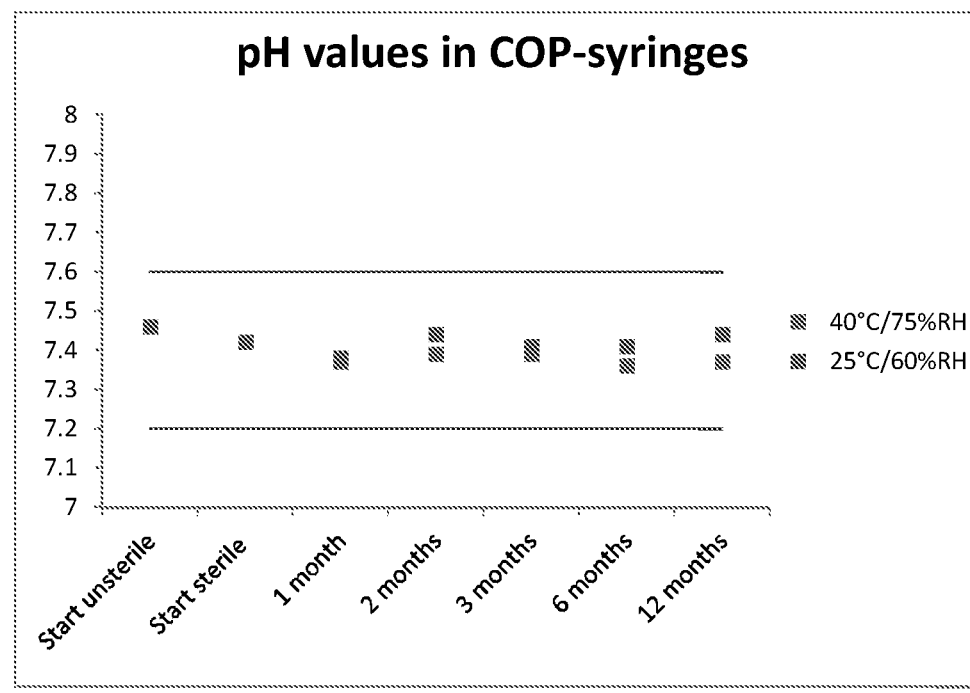
FIG. 7 shows the results of pH measurements at either 25° C./60% RH or 40° C./75% RH for up to 12 months in COP syringes.

FIG. 7 shows the results of pH measurements at either 25° C./60% RH or 40° C./75% RH for up to 12 months in COP syringes.

Figure 8:
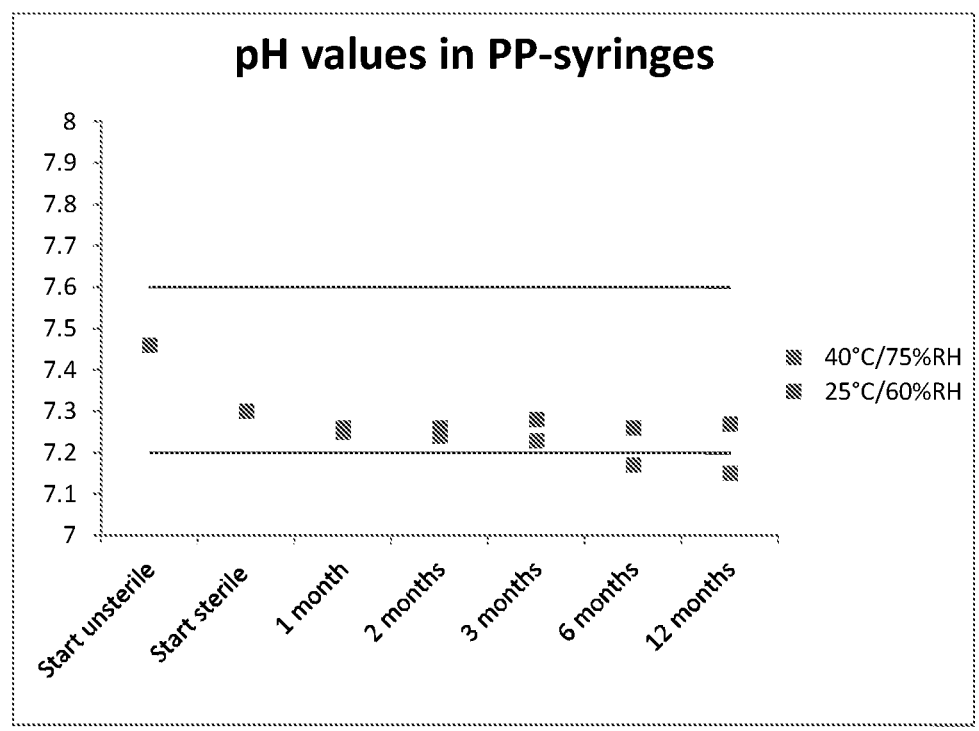
FIG. 8 shows the results of pH measurements at either 25° C./60% RH or 40° C./75% RH for up to 12 months in PP syringes.

FIG. 8 shows the results of pH measurements at either 25° C./60% RH or 40° C./75% RH for up to 12 months in PP syringes; the polypropylene syringes were not non-nucleated.

In conclusion, storage in COP syringes results in stability of the compositions including heparin, lidocaine and phosphate buffer, including stability of the pH values, the heparin concentration, the lidocaine concentration, and the existence of impurities, throughout the storage period for both storage at 25° C./60% RH and storage at 40° C./75% RH, although there is a slight loss of lidocaine during storage at 40° C./75% RH; this slight loss of lidocaine is not clinically significant for use of the compositions stored in COP syringes for treatment of urinary tract diseases and conditions such as interstitial cystitis. However, storage in PP syringes that are not non-nucleated resulted in a substantial loss of lidocaine; the loss of lidocaine occurred both at 25° C./60% RH and at 40° C./75% RH, although it was substantially greater at 40° C./75% RH.

This difference in stability between storage in COP syringes and PP syringes that are not non-nucleated is both unexpected and clinically significant. The increased stability of such compositions in COP syringes is important for the manufacture, storage, distribution, and use of these compositions, particularly for treatment of urinary tract diseases and conditions such as interstitial cystitis. The increased stability of the compositions provides for more accurate dosing and administration of the composition to a patient with such a urinary tract disease or condition without the risk of administering a dose less than an effective dose.

Table 9 shows the loss of lidocaine and the change in pH value after steam sterilization and subsequent transfer to a plastic syringe.

TABLE 9

| | Analyzing Urigen URG101 samples | | | |
|---|---|---|---|---|
| results: | Batch: 14068 (, 10 mM Sodium Phosphate) | pH value | lidocaine HCl assay % | loss of lidocaine HCl |
| | 1. glass vial | 7.41 | 1.32 | — |
| | 2. glass vial, steam sterilization | 7.39 | 1.32 | 0.0% |
| | 3. transfer to plastic syringe, steam sterilization | 7.12 | 1.19 | 9.8% |
| | Batch: RX501659.001 (, 28 mM Sodium Phosphate) | | | |
| | 1. glass vial | 7.54 | 1.35 | — |
| | 2. glass vial, steam sterilization | 7.56 | 1.35 | 0.0% |
| | 3. transfer to plastic syringe, steam sterilization | 1.35 | 1.15 | 14.8% |

Figure 9:
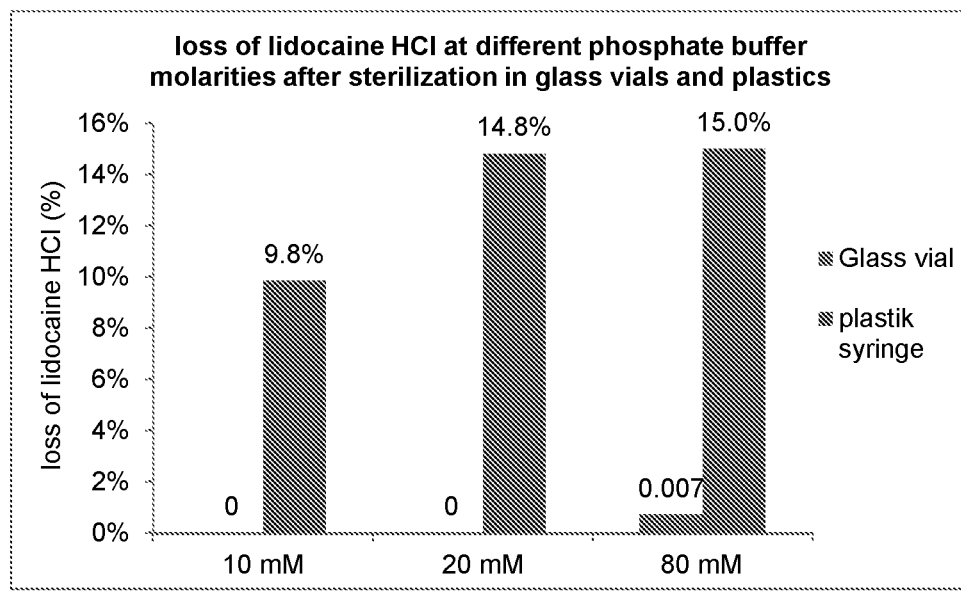
FIG. 9 shows the loss of lidocaine hydrochloride at different phosphate buffer molarities after sterilization in glass vials and polypropylene plastic syringes.

FIG. 9 shows the loss of lidocaine hydrochloride at different phosphate buffer molarities after sterilization in glass vials and plastic syringes. Except for a small loss at 80 mM phosphate buffer, there is no loss in glass vials, but there is a significant loss in plastic syringes, increasing with phosphate buffer molarity.

Additionally, the syringe parts (the plunger and the syringe body) were analyzed for leachables. The rubber and plastic parts (of a size that corresponds to real contact surfaces) in 11 mL solution glass containers (where no loss was observed) were tested for Tris and phosphate buffer formulations for 18 mL. The results are presented in Table 10. Table 10 shows that there is a loss of lidocaine hydrochloride in both materials, the rubber plunger and the plastic syringe body. There is a greater loss of lidocaine hydrochloride and a greater pH decrease in the syringe body than in the plunger. There is also a greater loss of lidocaine for the phosphate buffer formulation than for the Tris buffer formulation.

TABLE 10

Analyzing of the syringe parts (plunger and syringe body) for "leachables"

background: rubber and plastic parts (of a size that corresponds to real contact surface) in 11 mL solution glass containers (where no loss was observed)
tested for Tris and phosphate buffer formulation for 18 mL
results represent the average of double termination results:

|  | Tris buffer | | Phosphate buffer | |
| --- | --- | --- | --- | --- |
|  | plunger | syringe body | plunger | syringe body |
| pH value unsterile | 7.42 | 7.42 | 7.41 | 7.41 |
| Sterile after sterilization | 7.38 | 7.37 | 7.35 | 7.23 |
| lidocaine HCl assay unsterile % | 1.36 | 1.36 | 1.37 | 1.37 |
| lidocaine HCl assay sterile % | 1.34 | 1.30 | 1.30 | 1.19 |
| loss of lidocaine HCl | 1.1% | 4.4% | 4.8% | 13.2% |

-> loss of lidocaine HCl in both materials, rubber plunger and plastic syringe body
-> bigger loss of lidocaine HCl (and bigger pH value decrease) in syringe body than in plunger
-> bigger loss of lidocaine HCl (and bigger pH value decrease) in phosphate than in Tris buffer formulation Additionally, different extraction procedures were attempted to resolve the lidocaine from the plastic or rubber components of the syringes. For these procedures, 10× sterilized samples of the phosphate buffer formulations were used with >50% (>110 mg) loss of lidocaine hydrochloride. The syringe body and plunger were crushed and washed with solvent (55% acetonitrile, 45% water, pH 11, pH adjusted with NaOH); less than 0.02 mg of lidocaine hydrochloride could be resolved using this procedure. Other extraction agents were tested (tetrahydrofuran, ethanol, and water at pH 3, using extraction with a Soxhlet extractor for the syringe bodies. The results are shown in Table 11. The best extraction solvent is tetrahydrofuran (polypropylene syringes are unstable in tetrahydrofuran). However, only one-third of the missing lidocaine hydrochloride (112 mg) could be resolved.

TABLE 11

Extraction of the lidocaine out of the rubber and plastic parts background: different extraction tests to resolve the lidocaine from the plastic/rubber
10 x sterilized samples of phosphate buffer formulation was used with >50% (>110 mg) loss of idocaine HCl
1. syringe body and plunger crushed and washed with solvent (55% acetonitrile, 45% water pH 11 with NaOH)

TABLE 11-continued

Extraction of the lidocaine out of the rubber and plastic parts 2. other extractrion agents tested (tetrahydrofuran, ethanol, water pH3) with soxhlet extraction (only syringe bodies so far)

Figure 10:
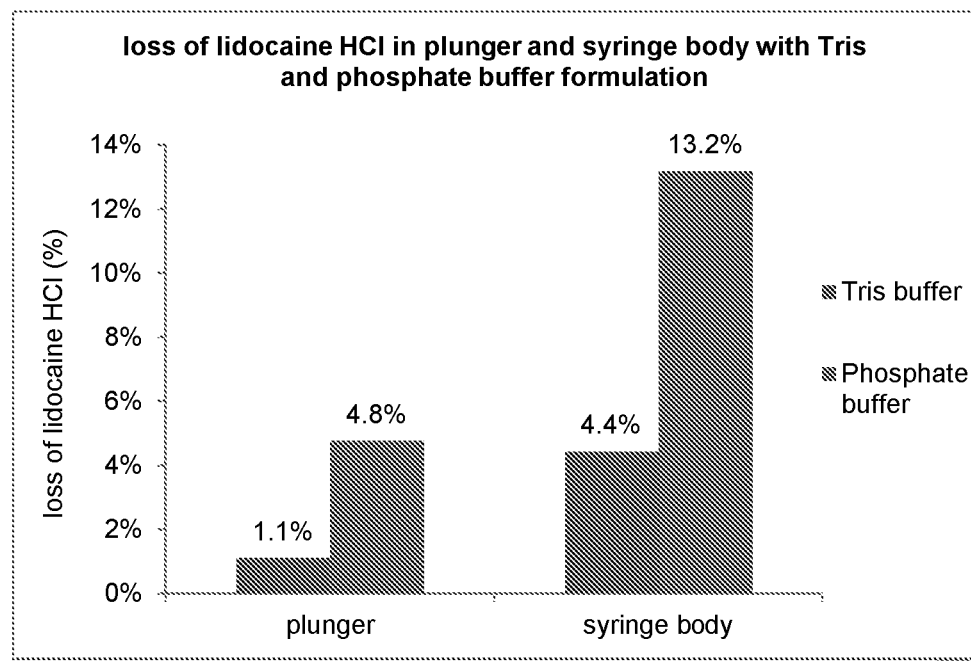
FIG. 10 shows the loss of lidocaine hydrochloride in the plunger and the syringe body with a Tris buffer formulation (left bar) and a phosphate buffer formulation (right bar).

| results: | THF | Ethanol | Water pH3 |
| --- | --- | --- | --- |
| extracted lidocaine/syringe (mg) | 30.41 | 17.56 | 9.98 |
| degradation peaks (incl. DMA) (% of the sum lidocaine peak area) | 4.67 | 5.62 | 24.81 |
| DMA (µg) | 32.55 | 2.16 | 56.76 | best extraction with THF (polypropylene syringes instable against THF)
but only <1/3 of the missing lidocaine (112 mg) could be resolved, plus some degradation products extraction of plunger FIG. 10 shows the loss of lidocaine hydrochloride in the plunger and the syringe body with a Tris buffer formulation (left bar) and a phosphate buffer formulation (right bar).

Figure 11:
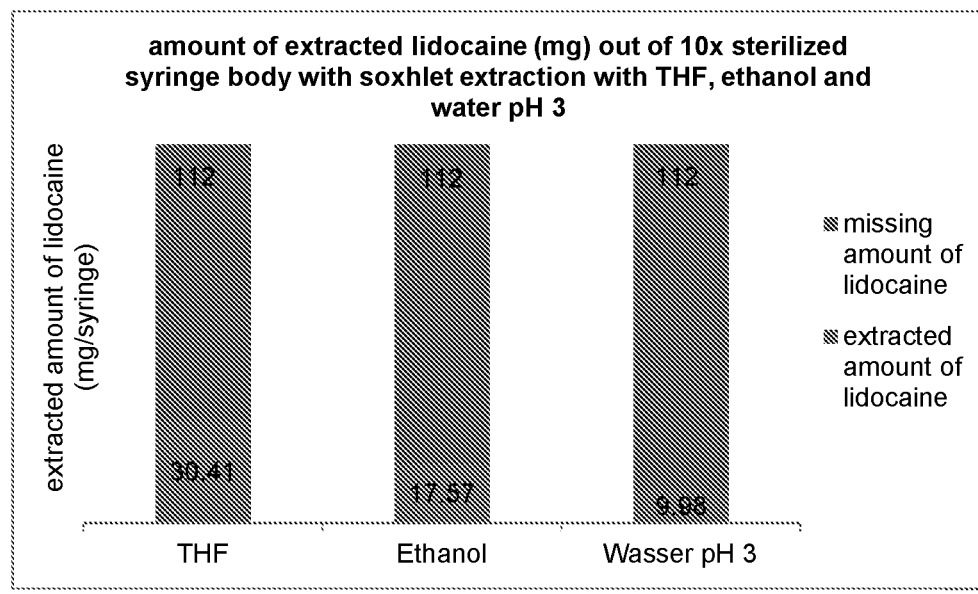
FIG. 11 shows the amount of extracted lidocaine hydrochloride using a Soxhlet extractor from a 10× syringe body using tetrahydrofuran (THF) (left bar), ethanol (central bar), and water at pH 3 (rightmost bar).

FIG. 11 shows the amount of extracted lidocaine hydrochloride using a Soxhlet extractor from a 10× syringe body using tetrahydrofuran (THF) (left bar), ethanol (central bar), and water at pH 3 (rightmost bar).

Table 12 shows pH dependency on the loss of lidocaine without (A) and with buffer (B); multiple sterilization rounds cause an additive effect (C).

TABLE 12

(A)
pH dependency no buffer

| 7/2/2014 Amount [g] | 7/15/2014 Amount [g] | 7/15/2014 Amount [g] | 7/2/2014 Amount [g] |
| --- | --- | --- | --- |
| 97.38 | 97.38 | 97.38 | 97.98 |
| 2.13 | 2.13 | 2.13 | 2.13 |
| 0.495 | 0.56 | 0.74 |  |
| 100.00 | 100.07 | 100.25 | 100.00 |
| 6.50 | 7.00 | 7.50 | 4.68 |
| 6.24 | 6.88 | 7.33 | 4.32 |
| 1.92 | 1.89 | 1.89 | 2.00 |
| 1.92 | 1.85 | 1.75 | 2.01 |
| 0.0% | 2.1% | 7.4% | −0.5% |

TABLE 12-continued (B)
pH dependency with buffer

| 7/2/2014 Amount [g] | 7/15/2014 Amount [g] | 7/15/2014 Amount [g] | 7/15/2014 Amount [g] | 7/15/2014 Amount [g] | 7/15/2014 Amount [g] |
|---|---|---|---|---|---|
| 97.65 | 97.44 | 96.81 | 97.00 | 95.70 | 95.70 |
| 2.13 | 2.13 | 2.13 | 2.13 | 2.13 | 2.13 |
| 0.015 | 0.030 | 0.450 | 0.060 | 0.070 | 0.122 |
| 0.2025 | 0.4050 | 0.6075 | 0.8100 | 2.663 | 0.951 |
|  |  |  |  |  | 0.830 |
| 100.00 | 100.00 | 100.00 | 100.00 | 100.56 | 99.73 |
| 6.74 | 7.11 | 7.17 | 7.27 | 7.40 | 7.40 |
| 6.43 | 6.87 | 6.97 | 7.10 | 7.27 | 7.21 |
| 2.00 | 1.99 | 2.14 | 1.95 | 1.97 | 1.97 |
| 1.94 | 1.83 | 1.93 | 1.69 | 1.59 | 1.70 |
| 3.0% | 8.0% | 9.8% | 13.3% | 19.3% | 13.7% |

(C)
Effect of multiple sterilizations

| | | Multiple sterilizations | | |
|---|---|---|---|---|
| | | pH value | Lidocaine HCl assay % (m/m) | loss of lidocaine |
| E | before Steril. | 7.19 | 1.98 | — |
| E1 | after 1. Steril. | 7.07 | 1.78 | 10.1% |
| E2 | after 2. Steril. | 6.98 | 1.66 | 16.2% |
| E3 | after 3. Steril. | 6.93 | 1.58 | 20.2% |
| E4 | after 4. Steril. | 6.84 | 1.46 | 26.3% |
| E5 | after 5. Steril. | 6.83 | 1.46 | 26.3% |
| E6 | after 6. Steril. | 6.74 | 1.32 | 33.3% |
| E7 | after 7. Steril. | 6.70 | 1.25 | 36.9% |
| E8 | after 8. Steril. | 6.70 | 1.26 | 36.4% |
| E9 | after 9. Steril. | 6.65 | 1.23 | 37.9% |
| E10 | after 10. Steril. | 6.61 | 1.18 | 40.4% |

Figure 12:
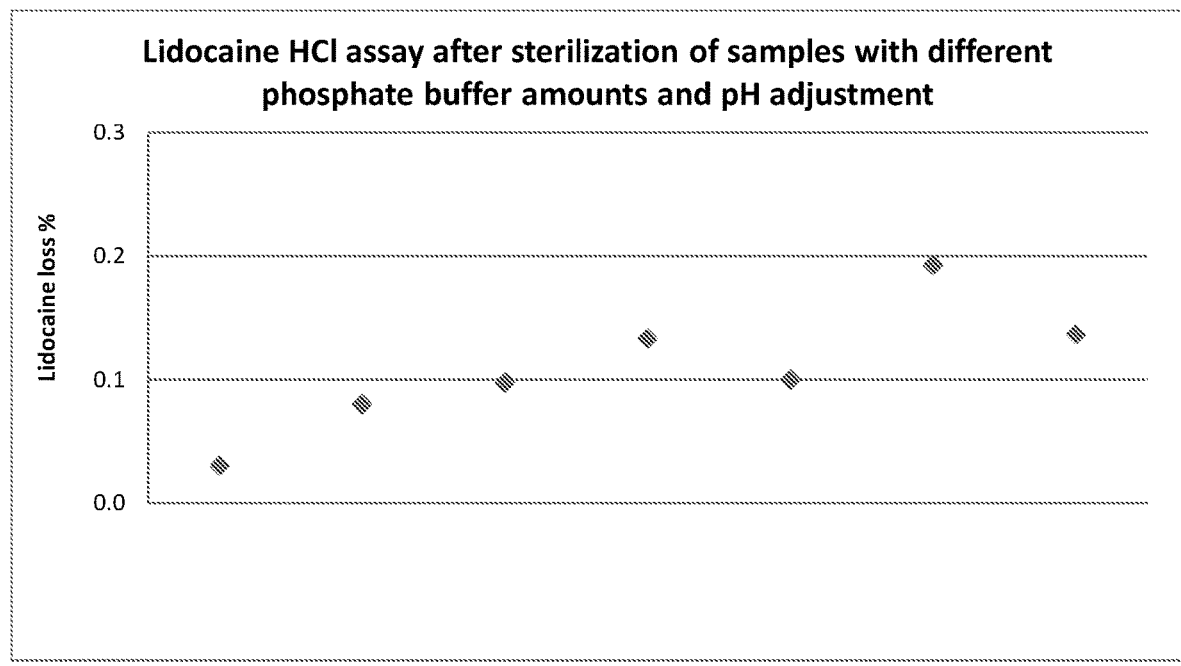
FIG. 12 shows the loss of lidocaine after sterilization of samples with different phosphate buffer amounts and pH adjustment, from the samples of Table 14(B).

FIG. 12 shows the loss of lidocaine after sterilization of samples with different phosphate buffer amounts and pH adjustment, from the samples of Table 14(B).

Figure 13:
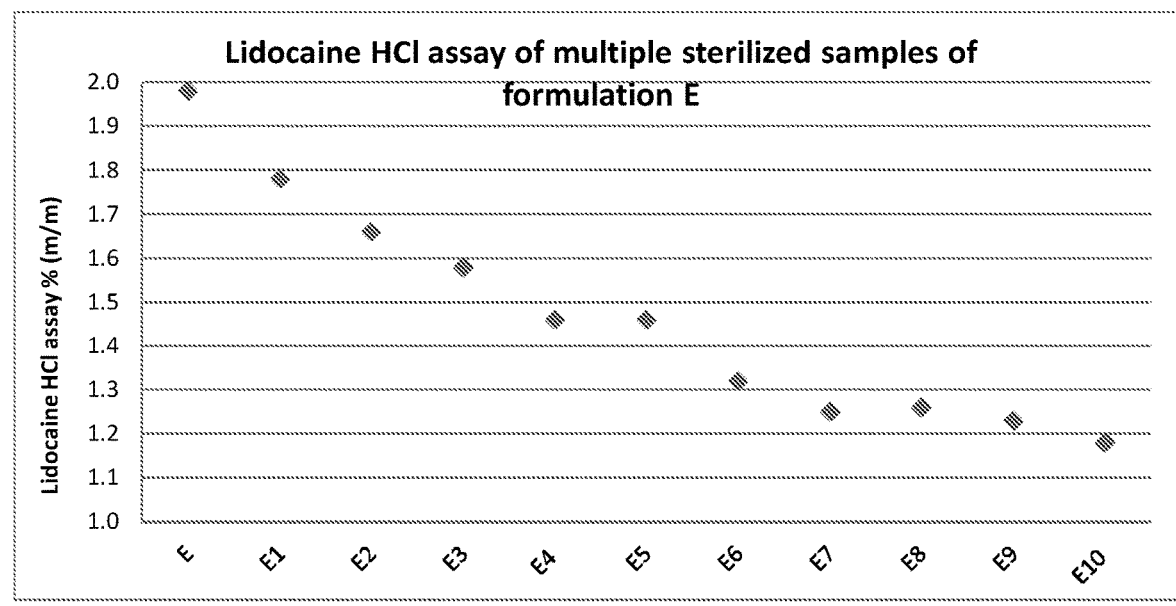
FIG. 13 shows the loss of lidocaine as a function of multiple rounds of sterilization, from the samples of Table 14(C).

FIG. 13 shows the loss of lidocaine as a function of multiple rounds of sterilization, from the samples of Table 14(C).

Table 13 shows the stability for up to 24 months of a preparation of lidocaine hydrochloride and heparin containing 200 mg of lidocaine hydrochloride and 50,000 units of heparin stored in a glass vial at 5° C.±3° C. and at ambient relative humidity (without prior sterilization).

TABLE 13

| Test & Method | Specifications | Test Results by Month | | | | | |
|---|---|---|---|---|---|---|---|
| | | Initial | One | Three | Six | Twelve | Twenty four |
| Appearance/ Visual | Clear, colorless to slightly yellow solution in clear glass vial with stopper and over seal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact |
| Heparin Anti-Factor IIa | 90%-110.0% of label claim | 106% | 99.0% | 98.6% | 87.4% | 99.6% | 104.8% |
| Heparin Anti-Factor Xa/IIa ratio | Anti-Factor Xa/Anti-Factor IIa ratio: 0.9-1.1 | 0.95 | 1.1 | 1.0 | 1.1 | 1.0 | 1.0 |
| Lidocaine Assay/UR-AN-001-R0 | 90.0%-110.0% of label claim | 101% | 99.0% | 100.2% | 100.0% | 100.1% | 102.8% |
| Lidocaine RS/UR-AN-002-R0 | Single largest impurity: NMT 0.2% Total impurities: NMT 0.5% | No impurities detected (LOD: 0.03%) | No impurities detected (LOD: 0.03%) | No impurities detected (LOD: 0.03%) | Impurity testing not performed at this point. | No impurities detected (LOD: 0.03%) | No impurities detected (LOD: 0.03%) |

TABLE 13-continued

| Test & Method | Specifications | Test Results by Month | | | | | |
|---|---|---|---|---|---|---|---|
| | | Initial | One | Three | Six | Twelve | Twenty four |
| pH/USP <791> | 7.4 ± 0.3 | 7.4 | 7.4 | 7.4 | 7.3 | 7.4 | 7.3 |

Table 14 shows the stability for up to 21 months of a preparation of lidocaine hydrochloride and heparin containing 200 mg of lidocaine hydrochloride and 50,000 units of heparin stored in a glass vial at 25° C.±2° C. and at relative humidity of 60%±5% (without prior sterilization).

TABLE 14

| Test & Method | Specifications | Test Results by Month | | | | | |
|---|---|---|---|---|---|---|---|
| | | Initial | One | Three | Six | Twelve | Twenty one |
| Appearance/ Visual | Clear, colorless to slightly yellow solution in clear glass vial with stopper and over seal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact |
| Heparin Anti-Factor IIa | 90%-110.0% of label claim | 106% | 116.0% | 106.6% | 93.0% | 103.7% | 104.1% |
| Heparin Anti-Factor Xa/IIa ratio | Anti-Factor Xa/Anti-Factor IIa ratio: 0.9-1.1 | 0.95 | 1.0 | 0.9 | 1.1 | 1.0 | 1.0 |
| Lidocaine Assay/UR-AN-001-R0 | 90.0%-110.0% of label claim | 101% | 98.7% | 99.7% | 100.4% | 100.5% | 102.9% |
| Lidocaine RS/UR-AN-002-R0 | Single largest impurity: NMT 0.2% Total impurities: NMT 0.5% | No impurities detected (LOD: 0.03%) | No impurities detected (LOD: 0.03%) | No impurities detected (LOD: 0.03%) | Impurity testing not performed at this point. | No impurities detected (LOD: 0.03%) | Single Largest impurity: 0.1% Total impurities: 0.1% |
| pH/USP <791> | 7.4 ± 0.3 | 7.4 | 7.4 | 7.4 | 7.3 | 7.4 | 7.3 |
| Sterility/ USP <71> | No Growth of Organisms | No growth observed | No growth observed | N/A | N/A | N/A | N/A |

Table 15 shows the stability for up to 21 months of a preparation of lidocaine hydrochloride and heparin containing 200 mg of lidocaine hydrochloride and 50,000 units of heparin stored in a glass vial at 40° C.±2° C. and at relative humidity of 75%±5% (without prior sterilization).

TABLE 15

| Test & Method | Specifications | Test Results by Month | | | | | |
|---|---|---|---|---|---|---|---|
| | | Initial[1] | One[2] | Three[3] | Six 4 | Twelve 5 | 21st 6 |
| Appearance/ Visual | Clear, colorless to slightly yellow solution in clear glass vial with stopper and over seal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact | Clear, colorless solution in clear glass vial with stopper and overseal intact |
| Heparin Anti-Factor IIa | 90%-110.0% of label claim | 106% | 116.0% | 106.6% | 93.0% | 103.7% | 104.1% |
| Heparin Anti-Factor Xa/Anti- | Anti-Factor Xa/Anti- | 0.95 | 1.0 | 0.9 | 1.1 | 1.0 | 1.0 |

TABLE 15-continued

| Test & Method | Specifications | Test Results by Month | | | | | |
|---|---|---|---|---|---|---|---|
| | | Initial[1] | One[2] | Three[3] | Six 4 | Twelve 5 | 21$^{st}$ 6 |
| Xa/IIa ratio | Factor IIa ratio: 0.9-1.1 | | | | | | |
| Lidocaine Assay/UR-AN-001-R0 | 90.0%-110.0% of label claim | 101% | 98.7% | 99.7% | 100.4% | 100.5% | 102.9% |
| Lidocaine RS/UR-AN-002-R0 | Single largest impurity: NMT 0.2% Total impurities: NMT 0.5% | No impurities detected (LOD: 0.03%) | No impurities detected (LOD: 0.03%) | No impurities detected (LOD: 0.03%) | Impurity testing not performed at this point. Client Notified | No impurities detected (LOD: 0.03%) | Single Largest impurity: 0.1% Total impurities: 0.1% |
| pH/USP <791> | 7.4 ± 0.3 | 7.4 | 7.4 | 7.4 | 7.3 | 7.4 | 7.3 |
| Sterility/ USP <71> | No Growth of Organisms | No growth observed | No growth observed | N/A | N/A | N/A | N/A |

Table 16 shows the loss of lidocaine and pH values for several preparations of heparin and lidocaine hydrochloride in glass syringes, polypropylene syringes, and high density polyethylene syringes.

TABLE 16

| Sample-Description | Sample (Terminally Sterilized) | Content [g/100 g] | Loss [%] | pH Value After Sterilization |
|---|---|---|---|---|
| PP-Syringe | Our Current PP Syringe | 1.25 | 12.0 | 7.07 |
| Ro-PP-Syringe | Spray Pattern SyringeRogalla | 1.18 | 16.9 | 6.93 |
| Schott Sterile | Schott Glass vial | 1.43 | 0 | 7.45 |
| Med 100 P | Material Med 100 in the form of pellets. Round. | 1.36 | 4.9 | 7.43 |
| Med 100 G | material Med 100 as Granulate | 0.99 | 30.8 | 7.11 |
| HD 6070 P | Material HD6070 in the form of pellets. Round. | 1.34 | 6.3 | 7.40 |
| HD 6070 G | Material HD6070 as Granulate | 0.83 | 42.0 | 6.96 |

Advantages of the Invention

The present invention provides improved articles of manufacture including a composition including a glycosaminoglycan, a local anesthetic, and a buffer packaged in a syringe; the syringe can be constructed of glass, cyclic olefin polymer (COP) or cyclic olefin copolymer (COC), or, alternatively, of high-density non-nucleated polypropylene. These improved articles of manufacture possess unexpectedly improved stability following terminal heat sterilization and long term storage, and the improved stability is important for the manufacture, storage, distribution, and use of these compositions, particularly for treatment of urinary tract diseases and conditions such as interstitial cystitis. The increased stability of the compositions provides for more accurate dosing and administration of the composition to a patient with such a urinary tract disease or condition without the risk of administering a dose that would be less than an effective dose.

Articles of manufacture according to the present invention possess industrial applicability as packaged compositions for the treatment of urinary tract diseases such as, but not limited to, interstitial cystitis.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Moreover, the transitional phrase "comprising" is intended to encompass the transitional phrases "consisting essentially of" and "consisting of" unless the terms "consisting essentially of" and "consisting of" are clearly excluded, either expressly or by context. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. An article of manufacture comprising a heat sterilized aqueous liquid composition including:
   (a) an anionic polysaccharide, selected from the group consisting of:
   hyaluronic acid, chondroitin sulfate, pentosan polysulfate, dermatan sulfate, heparin, heparan sulfate, and keratan sulfate;
   (b) a local anesthetic, wherein the local anesthetic is lidocaine; and
   (c) a buffer selected from the group consisting of phosphate buffer, bicarbonate buffer, Tris (Tris(hydroxymethyl)aminomethane) buffer, MOPS buffer (3-(N-morpholino)propanesulfonic acid), HEPES (N-(2-hydroxyethyl)piperazine-N-(2-ethanesulfonic acid) buffer, ACES (2-[(2-amino-2-oxoethyl)amino]ethanesulfonic acid) buffer, ADA (N-(2-acetamido)2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid) buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS (N-(2-hydroxyethylpiperazine)-N'-(3-propanesulfonic acid) buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropaneulfonic acid) buffer, TAPS (N-tris[hydroxymethyl]methyl-3-aminopropanesulfonic acid) buffer; TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, and a combination thereof, wherein the components of (a), (b), and (c) form a composition; and
   (d) a container comprising a syringe or vial that is compatible with heat sterilization or sterilization by autoclaving, wherein the container packages the composition formed by the components of (a), (b), and (c), wherein the container is selected from the group consisting of glass and a plastic selected from the group consisting of cyclic olefin polymer plastic, cyclic olefin copolymer plastic, high density polyethylene, and high density non-nucleated polypropylene;
   wherein the pH of the composition is between 6.8 and 8.2 and local anesthetic is stable through the sterilization process and after 12 months of storage such that at least 95% of the lidocaine originally present in the composition is present after 12 months of storage.

2. The article of manufacture of claim 1 wherein the heparinoid is heparin and wherein the heparin is heparin sodium.

3. The article of manufacture of claim 1 wherein a unit dose of the composition included in the article of manufacture comprises from about 1000 units of heparin to about 250,000 units of heparin per unit dose of the composition.

4. The article of manufacture of claim 1 wherein a unit dose of the composition included in the article of manufacture comprises about 40,000 units of heparin, about 50,000 units of heparin, or about 60,000 units of heparin.

5. The article of manufacture of claim 1 wherein the lidocaine is lidocaine hydrochloride.

6. The article of manufacture of claim 1 wherein a unit dose of the composition included in the article of manufacture comprises a quantity of lidocaine of from about 10 mg to about 400 mg of lidocaine per unit dose of the composition.

7. The article of manufacture of claim 6 wherein a unit dose of the composition included in the article of manufacture comprises 10 mL of 1% lidocaine or 16 mL of 2% lidocaine.

8. The article of manufacture of claim 1 wherein the buffer is selected from the group consisting of phosphate buffer, bicarbonate buffer, Tris buffer, and a combination thereof.

9. The article of manufacture of claim 8 wherein the buffer is phosphate buffer and wherein the phosphate buffer is sodium phosphate buffer.

10. The article of manufacture of claim 8 wherein the buffer is bicarbonate buffer and wherein the bicarbonate buffer is sodium bicarbonate buffer.

11. The article of manufacture of claim 8 wherein the buffer is Tris buffer.

12. The article of manufacture of claim 1 wherein the composition included in the article of manufacture comprises an additional component selected from the group consisting of:
   (a) an osmolar component that provides an isotonic or nearly isotonic solution compatible with human cells and blood;
   (b) a compound that enables persistence of the composition to the surface of the bladder epithelium in a quantity sufficient to treat, ameliorate, or prevent a lower urinary tract disorder;
   (c) an antibacterial agent in a quantity sufficient to treat, ameliorate, or prevent a lower urinary tract disorder;
   (d) an antifungal agent in a quantity sufficient to treat, ameliorate, or prevent a lower urinary tract disorder;
   (e) a vasoconstrictor in a quantity sufficient to treat, ameliorate, or prevent a lower urinary tract disorder;
   (f) a preservative; and
   (g) an anti-inflammatory agent.

13. The article of manufacture of claim 1 wherein the pH of the composition included in the article of manufacture is from about 7.2 to about 7.6.

14. The article of manufacture of claim 13 wherein the pH of the composition included in the article of manufacture is about 7.5.

15. The article of manufacture of claim 1 wherein the composition included in the article of manufacture is formulated for treating a lower urinary tract disorder selected from the group consisting of bacterial cystitis, fungal/yeast cystitis, vulvar vestibulitis, vulvodynia, dyspareunia, urethral syndrome, and endometriosis in women; prostatitis and chronic pelvic pain syndrome in men; and radiation-induced cystitis, chemotherapy-induced cystitis, interstitial cystitis (bladder pain syndrome or hypersensitive bladder syndrome), and overactive bladder in men or women.

16. The article of manufacture of claim 15 wherein the composition included in the article of manufacture is formulated for treating interstitial cystitis (bladder pain syndrome or hypersensitive bladder syndrome).

17. The article of manufacture of claim 1 wherein the syringe or vial is constructed of glass.

18. The article of manufacture of claim 1 wherein the syringe or vial is constructed of a plastic selected from the group consisting of cyclic olefin polymer plastic, cyclic olefin copolymer plastic, high density polyethylene, and high density non-nucleated polypropylene.

19. The article of manufacture of claim 1 wherein the syringe or vial is a syringe.

20. The article of manufacture of claim 19 wherein the interior of the barrel of the syringe is coated to reduce deposition of the local anesthetic on the syringe.

21. The article of manufacture of claim 20 wherein the coating is a siloxane coating deposited by a plasma deposition process.

* * * * *